United States Patent
Ito et al.

(10) Patent No.: US 10,808,333 B2
(45) Date of Patent: Oct. 20, 2020

(54) METHOD AND APPARATUS FOR PERFORMING LAYOUT DESIGNS USING STEM CELLS

(71) Applicant: TOTIC TECHNOLOGY INC., Morgan Hill, CA (US)

(72) Inventors: Choshu Ito, San Mateo, CA (US); Dan Bui, Sunnyvale, CA (US)

(73) Assignee: Totic Technology Inc., Morgan Hill, CA (US)

( * ) Notice: Subject to any disclaimer, the term of this patent is extended or adjusted under 35 U.S.C. 154(b) by 0 days.

(21) Appl. No.: 16/242,554

(22) Filed: Jan. 8, 2019

(65) Prior Publication Data
US 2019/0211475 A1    Jul. 11, 2019

Related U.S. Application Data

(60) Provisional application No. 62/614,727, filed on Jan. 8, 2018.

(51) Int. Cl.
| | | |
|---|---|---|
| *G06F 30/00* | (2020.01) | |
| *C40B 40/02* | (2006.01) | |
| *C12N 5/0735* | (2010.01) | |
| *G06F 30/36* | (2020.01) | |
| *G06F 30/39* | (2020.01) | |
| *G06F 30/327* | (2020.01) | |
| *G06F 30/392* | (2020.01) | |
| *G06F 30/394* | (2020.01) | |
| *H01L 27/11* | (2006.01) | |
| *H01L 27/118* | (2006.01) | |

(52) U.S. Cl.
CPC ............ *C40B 40/02* (2013.01); *C12N 5/0606* (2013.01); *G06F 30/327* (2020.01); *G06F 30/36* (2020.01); *G06F 30/39* (2020.01); *G06F 30/392* (2020.01); *G06F 30/394* (2020.01); *H01L 27/1104* (2013.01); *H01L 27/11807* (2013.01)

(58) Field of Classification Search
CPC . G06F 17/505; G06F 17/5063; G06F 17/5072
USPC ...................................................... 716/119
See application file for complete search history.

(56) References Cited

U.S. PATENT DOCUMENTS

| | | | | |
|---|---|---|---|---|
| 2009/0199136 A1* | 8/2009 | Reis | ....................... | G06F 30/30 716/132 |
| 2013/0047127 A1* | 2/2013 | Arunachalam | ..... | G06F 17/5072 716/103 |
| 2015/0143314 A1* | 5/2015 | Chen | ................... | G06F 17/5081 716/112 |
| 2015/0269302 A1* | 9/2015 | Katta | .................. | G06F 17/5072 716/120 |

(Continued)

*Primary Examiner* — Suchin Parihar
(74) *Attorney, Agent, or Firm* — Blue Capital Law Firm, P.C.

(57) ABSTRACT

A method and system for designing an integrated circuit layout are disclosed. In one embodiment, the method includes generating a stem cell library with stem cell layouts, wherein each stem cell layout includes an analog core area where a device element resides, and abutment boundaries on left, right, top, and bottom sides of the analog core area. The method also includes mapping device elements in a schematic netlist to the stem cell layouts in the stem cell library. In addition, the method includes placing and routing the mapped device elements to optimize a layout for the schematic netlist.

20 Claims, 31 Drawing Sheets
(16 of 31 Drawing Sheet(s) Filed in Color)

Block-Level Layout Optimization Flow

(56) References Cited

U.S. PATENT DOCUMENTS

| | | | | |
|---|---|---|---|---|
| 2015/0302128 A1* | 10/2015 | Katta | ................ | G06F 17/5072 |
| | | | | 716/120 |
| 2017/0212978 A1* | 7/2017 | Ethirajan | ............ | G06F 17/5081 |
| 2017/0345809 A1* | 11/2017 | Chang | ................ | H01L 27/0207 |
| 2018/0156869 A1* | 6/2018 | Wohl | ...................... | G06F 17/50 |
| 2018/0166433 A1* | 6/2018 | Fujiwara | ................ | G06F 17/50 |
| 2018/0341742 A1* | 11/2018 | Yazdani | .............. | G06F 17/5081 |

\* cited by examiner

Block-Level Layout Optimization Flow

Pareto plot - Each point is a layout choice with different metric.

Detailed Layout Optimization Flow

METHOD AND APPARATUS FOR PERFORMING LAYOUT DESIGNS USING STEM CELLS

CROSS-REFERENCE TO RELATED APPLICATIONS

The present Application claims the benefit of U.S. Provisional Patent Application Ser. No. 62/614,727 filed on Jan. 8, 2018, the entire disclosure of which is incorporated herein in its entirety by reference.

FIELD

This disclosure generally relates to Electronic Computer-Aided Design (ECAD), and more particularly, to a method and apparatus for performing layout designs using Stem Cells.

BACKGROUND

In one aspect, the present invention innovates in the area of analog/mixed-signal layout automation in integrated circuit design. Traditionally, analog/mixed-signal layout is a manual process, where design engineers place polygons for different layers to construct layouts using pcells. The polygon placements are constrained by design rules, which have become exponentially more complex at recent technology nodes. As a result, both the engineering man-hours and overall time to delivery have suffered. In one aspect, an objective of the present invention is to dramatically improve this layout effort problem by developing a new methodology for analog/mixed-signal layout that dramatically reduces the required engineering man-hours and schedule.

SUMMARY

A method and system for designing an integrated circuit layout are disclosed. In one embodiment, the method includes generating a stem cell library with stem cell layouts, wherein each stem cell layout includes an analog core area where a device element resides, and abutment boundaries on left, right, top, and bottom sides of the analog core area. The method also includes mapping device elements in a schematic netlist to the stem cell layouts in the stem cell library. In addition, the method includes placing and routing the mapped device elements to optimize a layout for the schematic netlist.

BRIEF DESCRIPTION OF THE DRAWINGS

This application contains at least one drawing executed in color. Copies of this patent application with color drawings will be provided by the Office upon request and payment of the necessary fee. The color drawings are being filed electronically via EFS-Web, only one set of drawings is submitted.

DETAILED DESCRIPTION

Figure 1:
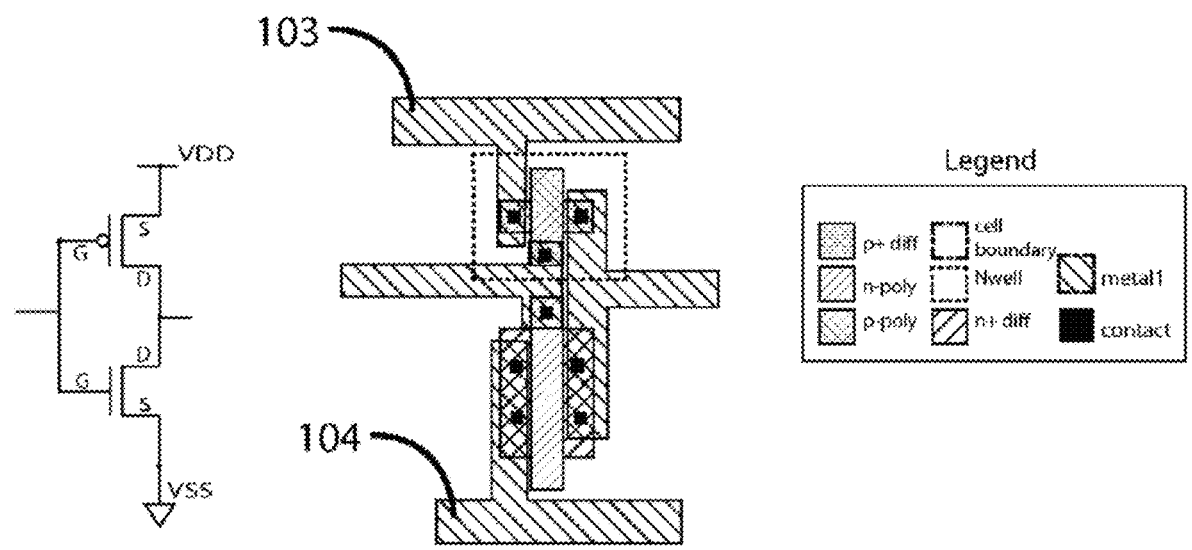
FIG. 1 shows an exemplary digital standard cell, an inverter, drawn as a transistor-level schematic on the left and as a layout-level (physical design) schematic on the right.

One aspect of the methodology of designing SoCs is to utilize a library of digital standard cells to layout the physical design. A digital standard cell is generally comprised of a few transistors that perform some logic function. The logic function is typically elementary or simple, for example a logical AND function, a logical OR function, and so on. The left side of FIG. 1 shows an typical CMOS inverter (logical NOT function) and the right side of FIG. 1 shows a corresponding digital standard cell with connections made to the VDD and VSS power rails. By interconnecting the inputs and outputs of multiple digital standard cells, more complex logic functions can be created, thereby forming building blocks of an SoC physical design.

ECAD tools are used to select standard cells from a library, map the circuitry of an SoC design to standard cells, place standard cells, and route (interconnect) standard cells to create the physical design (the layout). ECAD tools generally place and route standard cells based on some predefined constraints, such as the timing of electrical signals between standard cells or minimization of layout area. Placement refers to the physical positioning of a standard cell within an SoC layout and routing refers to the determination of conductive interconnects between such cells. Modern ECAD tools are very efficient in place and route operations, which has resulted in an enormous productivity boost in the physical design flow of digital SoCs. A billion-transistor SoC design may be laid out using this ECAD-based standard cell methodology within a few months. Whereas digital designer productivity is currently measured in millions of transistors placed per day, state-of-the-art analog designer productivity is currently measured in only tens of transistors per day. This orders-of-magnitude productivity gap is the direct result of decades of advancements made in the place-and-route efficiency of ECAD tools.

Figure 2:
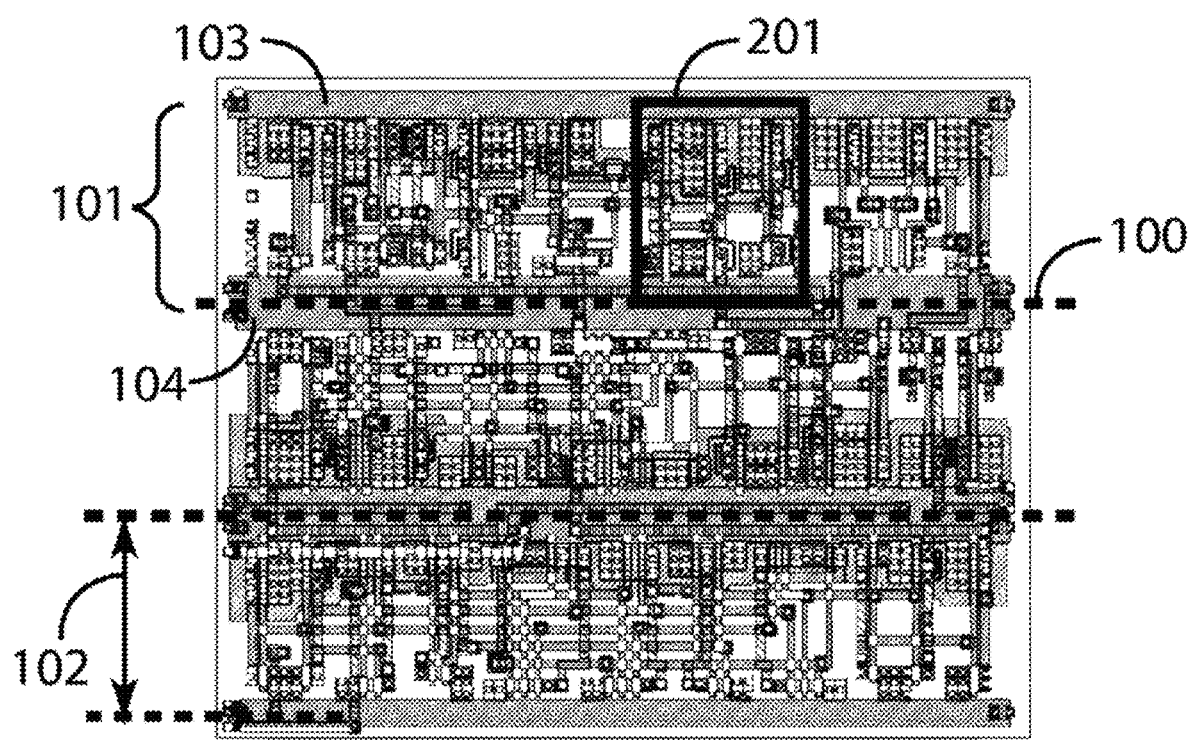
FIG. 2 shows an exemplary two-dimensional row-based grid system that is common in the SoC design environment, and the placement of a number of digital standard cells therein according to one embodiment.

ECAD tools generally place standard cells in an SoC physical design based on a two-dimensional row-based grid 100 as shown in FIG. 2. Each row 101 within the grid 100 are traditionally oriented horizontally and considered to have a predetermined row height 102 (the same grid-based layout concept applies equally to a fixed-width column-based grid). At the row 101 boundaries may be routed a VDD (Voltage Drain Drain) power rail 103 and a VSS (Voltage Source Source) power rail 104, which is typically done using a metal layer such as metal 1 or metal 2. A placed standard cell is appropriately connected to such VDD power rail 103 and VSS power rail 104 to provide power to the cell, as was shown in FIG. 1.

Figure 3:
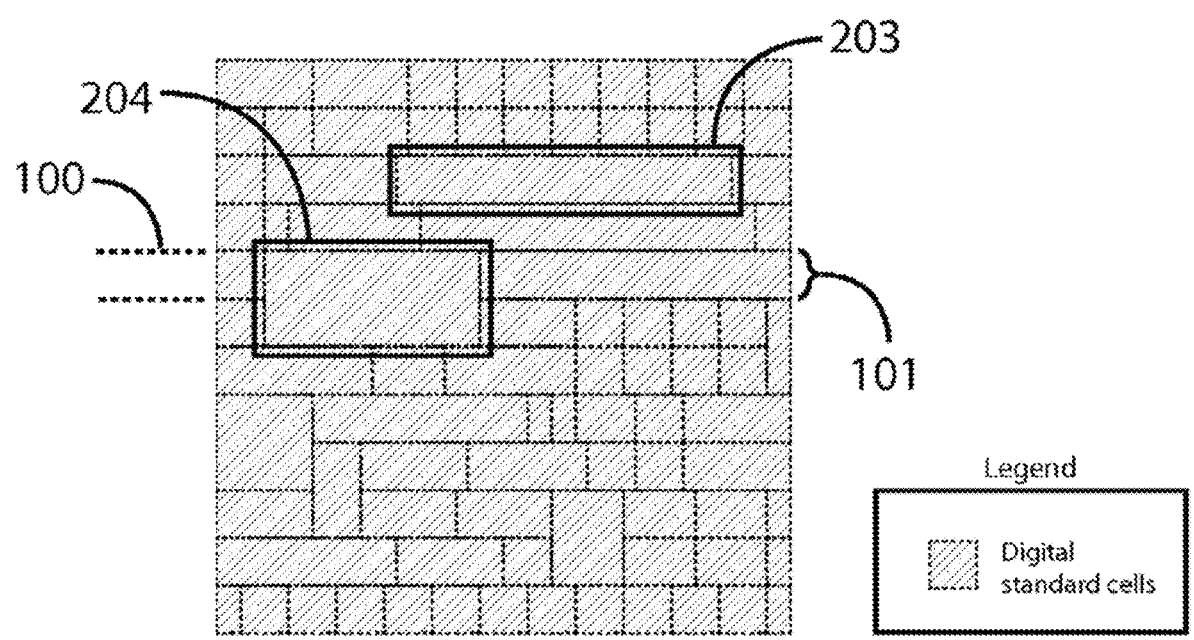
FIG. 3 shows an exemplary two-dimensional row-based grid system of a digital SoC in which row-height and integer-multiple row-height digital standard cells are placed according to one embodiment.

While the standard cells within a library may have varying (typically integer-multiple) physical height dimensions, a critical element to ECAD tools' efficiency has been for an ECAD tool to select from a library only standard cells with the same height dimension for placement within a particular row. This constraint greatly reduces the complexity of the physical design space and makes the placement and routing of an enormous number of cells possible. An example of multiple digital standard cells 201 placed within rows 101 of a grid 100 is shown in FIG. 3.

This row-based placement methodology does not necessarily mean that all the rows of the SoC are of the same height, although in practice this is almost always the case. As long as the standard cells can fit into an integer-multiple of the grid row height, the constraint is not violated. FIG. 3 shows an exemplary placement of single-row digital cells 203 and double-row digital cells 204 within the rows 101 of a grid 100.

Figure 4:
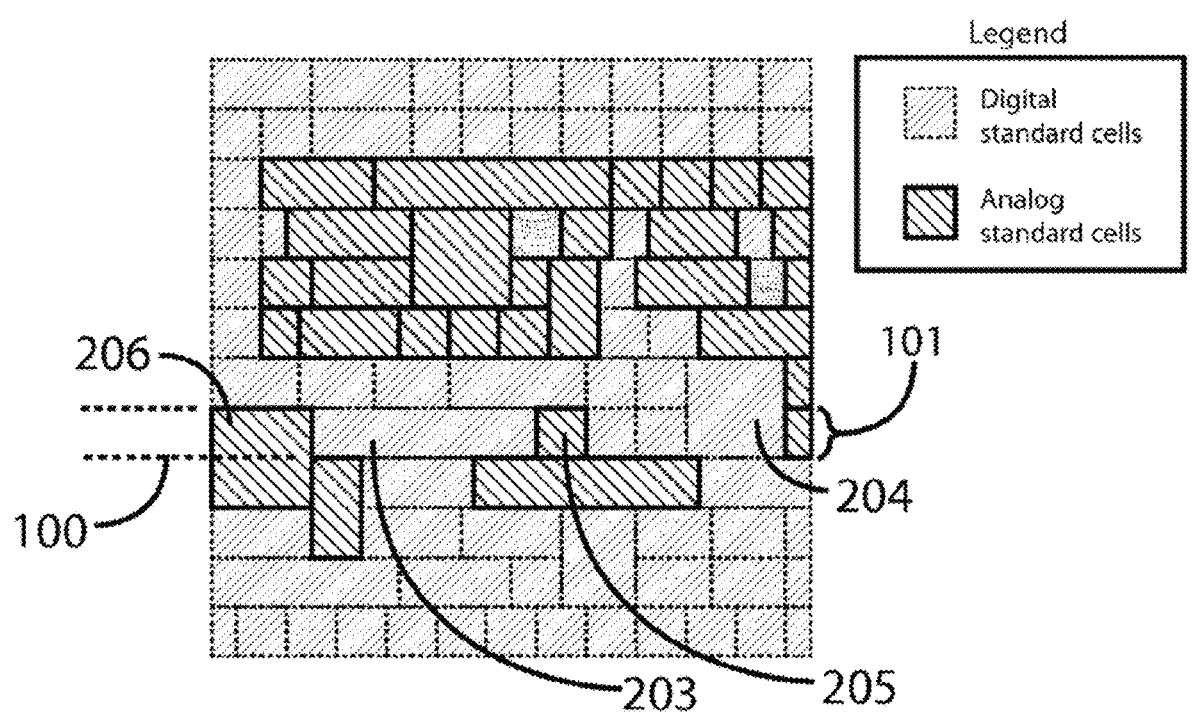
FIG. 4 shows an exemplary two-dimensional row-based grid system of a mixed-signal SoC in which row-height and integer-multiple row-height digital standard cells, and row-height and integer-multiple row-height analog standard cells, are placed according to one embodiment.

When both digital and analog standard cells are similarly constrained by row height, there may be no substantial distinction between digital standard cells and analog standard cells in the ECAD design environment—both may be placed and routed according to similar constraint-based metrics, for example timing of electrical signals between standard cells or minimization of layout area. An ECAD tool can place both types of cells in any suitably distributed manner rather than the current state-of-the-art practice of placing digital cells in one area of the SoC layout and analog cells in another. FIG. 4 shows an example of this flexible placement methodology wherein single-row digital cells 203, single-row analog cells 205, double-row digital cells 204, and double-row analog cells 206 are distributed within the rows 101 of a grid 100.

Also, unlike the designer-adjustable parameters of a pcell, each analog standard cell has a fixed set of parameters and thus a fixed layout. Fixing the layout parameters of an analog standard cell gives such cell a specific function, which can be as simple as the gating function of a single transistor or a more complex function like that of a current source. The library may contain many analog standard cells of a particular type, for example multiple current source analog standard cells with differing parameters, for example different current drive strengths. In other words, there may be a family of current source analog standard cells within a library. In one embodiment, an analog standard cell type, and related variants thereof, could be used to describe a family of analog standard cells of the specified type, wherein a family may have zero or more members.

Figure 6A:
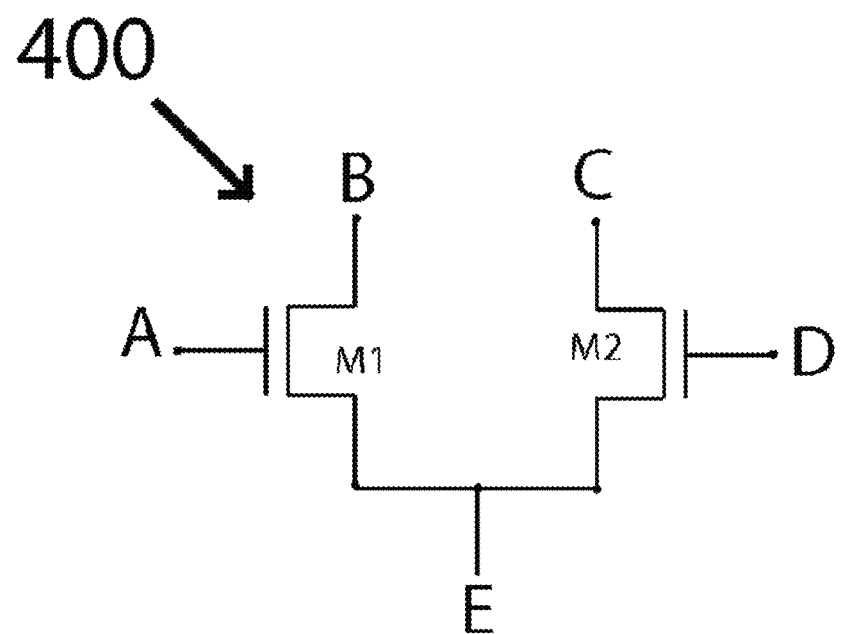
FIG. 6a shows an exemplary transistor-level differential pair circuit according to one embodiment.
Figure 6B:
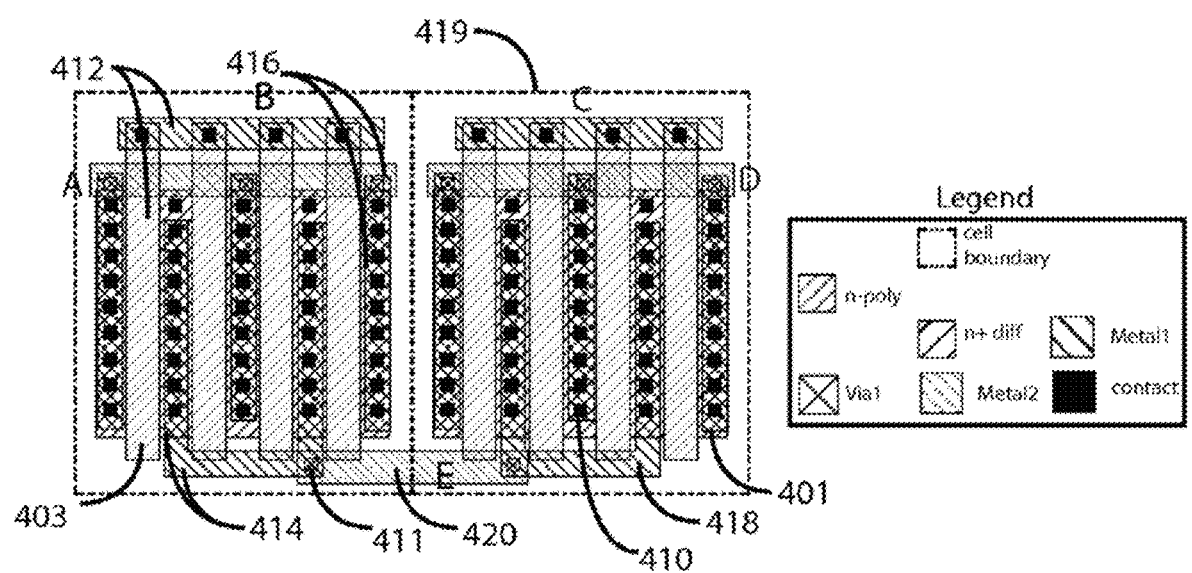
FIG. 6b shows a corresponding exemplary layout-level analog standard cell according to one embodiment.
Figure 7A:
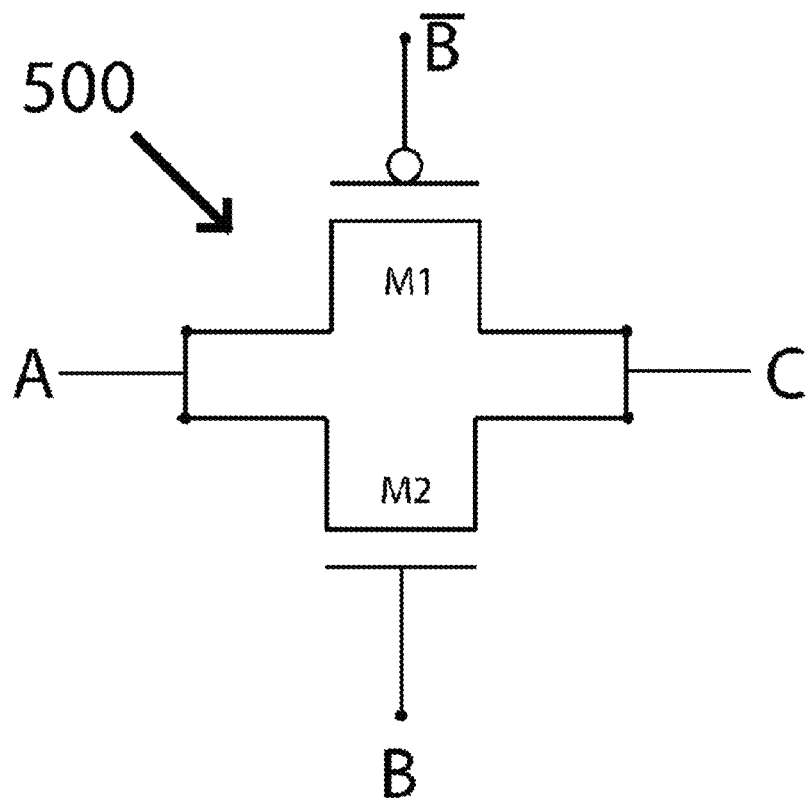
FIG. 7a shows an exemplary transistor-level pass gate circuit according to one embodiment.
Figure 7B:
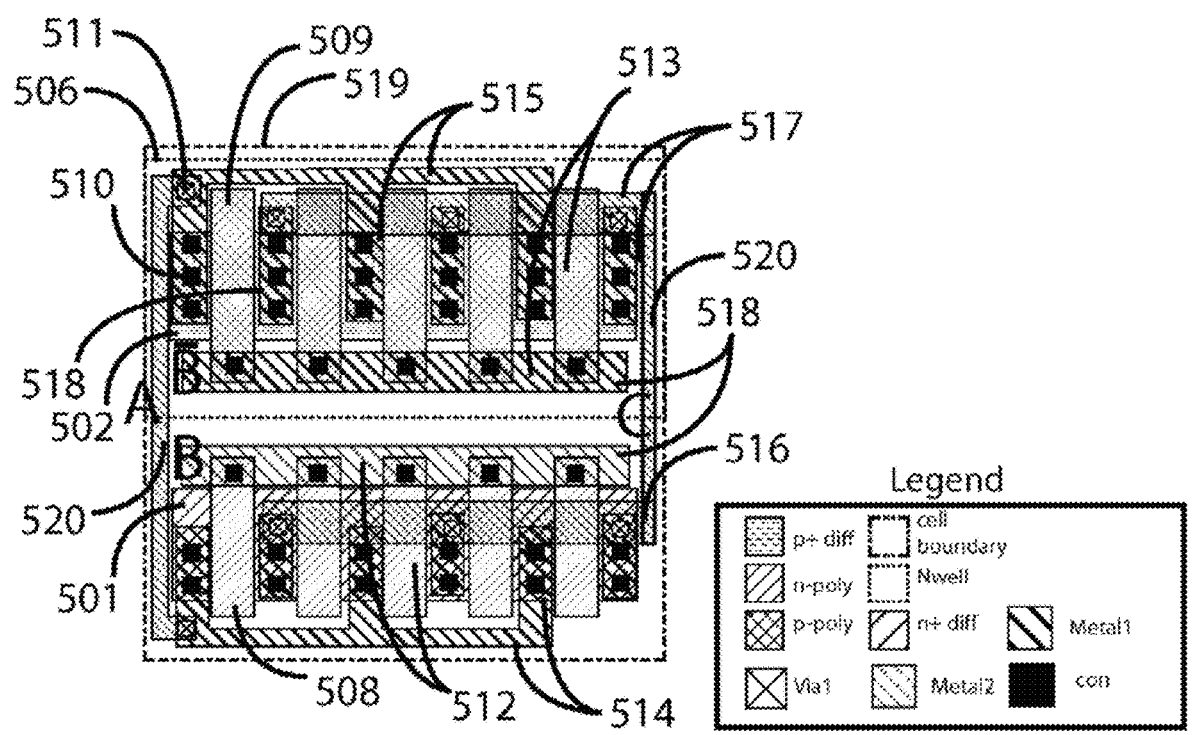
FIG. 7b shows a corresponding exemplary layout-level analog standard cell implemented using a single general type analog standard cell according to one embodiment.

The utility of an analog standard cell library may be defined in part by the ability, efficiency, and speed that an ECAD tool can select, place, and route analog standard cells from such library to design an analog or mixed-signal SoC. Generally, a library containing more types of analog standard cells, and with more parametric variations of a particular type of analog standard cell, has greater utility. Examples of analog standard cell types of a library may include, but are not limited to, general types, differential pairs, moscaps, varactors, resistors, current sources, current mirrors, well-taps, and ESD devices. With the exception of the general type, which will be described shortly, the names of these exemplary types of analog standard cells imply corresponding analog functions and physical layouts that are well-known in the art. Thus, these non-general analog standard cell examples will not be detailed further, with the exception of a brief layout-level description of an exemplary differential pair (as shown in FIG. 6a and FIG. 6b) and an exemplary pass gate (as shown in FIG. 7a and FIG. 7b).

The general type analog standard cell could be a family of cells that may implement NMOS and PMOS transistors of differing parameters. In one embodiment, a parameter, when applied to analog standard cells, could be used generally to mean any parameter or feature that may alter some property of the cell. Increasing the effective channel width or length of a transistor within a standard cell is an example parametric variation that yields a readily observable property variation—transistor drive strength. Duplicating (doubling-up) one or more vias within a cell is an example parametric variation that yields a less readily observable property variation—manufacturing yield (Design for Manufacturing (DFM)). Other general type analog standard cell parameters that may be varied include, but are not limited to, contacts on both sides of poly fingers, non-uniform sizes and/or spacing of poly fingers, non-vertically aligned n-type poly fingers to p-type poly fingers, number of contacts to diffusion regions, spacing between diffusion regions, and metal line widths.

Figure 5A:
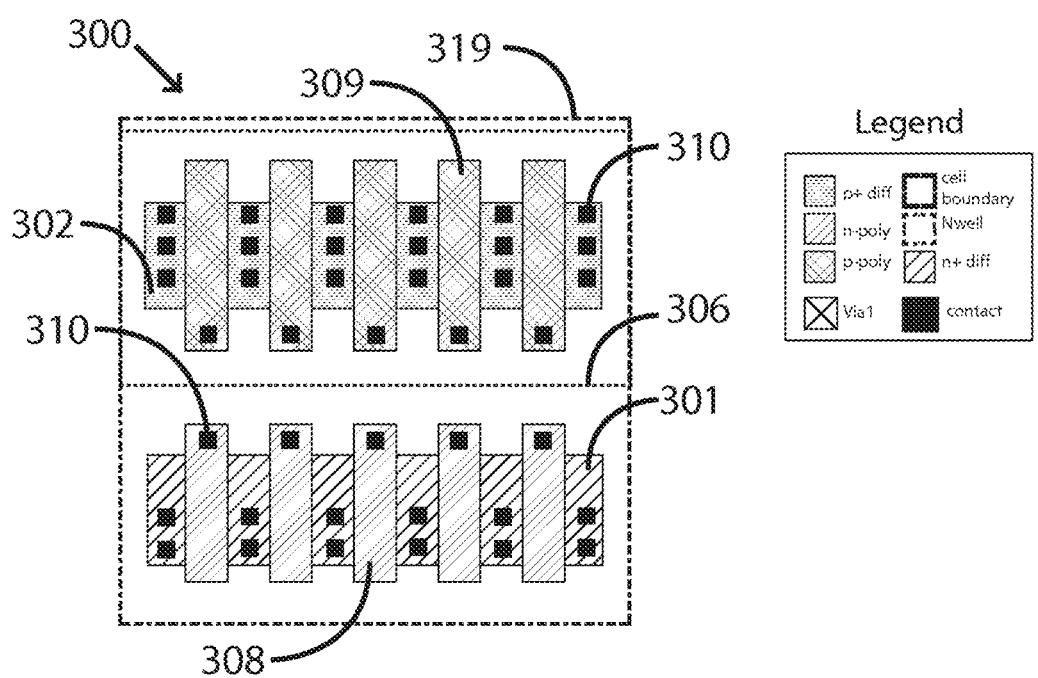
FIG. 5a shows the preliminary layout-level structure of an exemplary general type analog standard cell prior to metallization according to one embodiment.

FIG. 5a shows an exemplary layout-level, partially implemented general cell 300 in which the parameter to be varied is effective channel width of an NMOS transistor and effective channel width of a PMOS transistor (varied independently), each of which alters each transistor's drive strength property. Within its cell boundary 319 is included an nwell 306, a p-type diffusion 302, and an n-type diffusion 301. Alternatively or in addition, multiple n-type and p-type wells may be included depending on the fabrication process used to manufacture the SoC, for example if the n-type or p-type substrate is used. For this particular example, there are a maximum of 5 NMOS fingers 308 spanning the n-type diffusion 301 and 5 PMOS fingers 309 spanning the p-type diffusion 302. Alternatively, the general cell 300 may be implemented with more or less total fingers, and the number of NMOS fingers 308 need not be equal to the number of PMOS fingers 309.

The NMOS and PMOS transistors of the exemplary partially implemented general cell 300 of FIG. 5a can each assume a variable effective channel width, in normalized units, of 0, 1, 2, 3, 4, or 5. Consequently, a library containing this exemplary 5-NMOS-finger and 5-PMOS-finger general type analog standard cell may include cells with NMOS and PMOS transistors of effective channel widths, respectively and in arbitrary units, of "0 and 1", "0 and 2", "0 and 3", "0 and 4", "0 and 5", "1 and 0", "1 and 1", "1 and 2", and so on up to "5 and 5". Excluding the "0 and 0" cell there are 35 such exemplary 5-NMOS-finger and 5-PMOS-finger general type analog standard cells that could be included in the library. In general, excluding the 0-width NMOS and 0-width PMOS configuration ("0 and 0"), a general cell 300 with N NMOS fingers and P PMOS fingers has N.times.P−1 possible configurations.

Figure 5B:
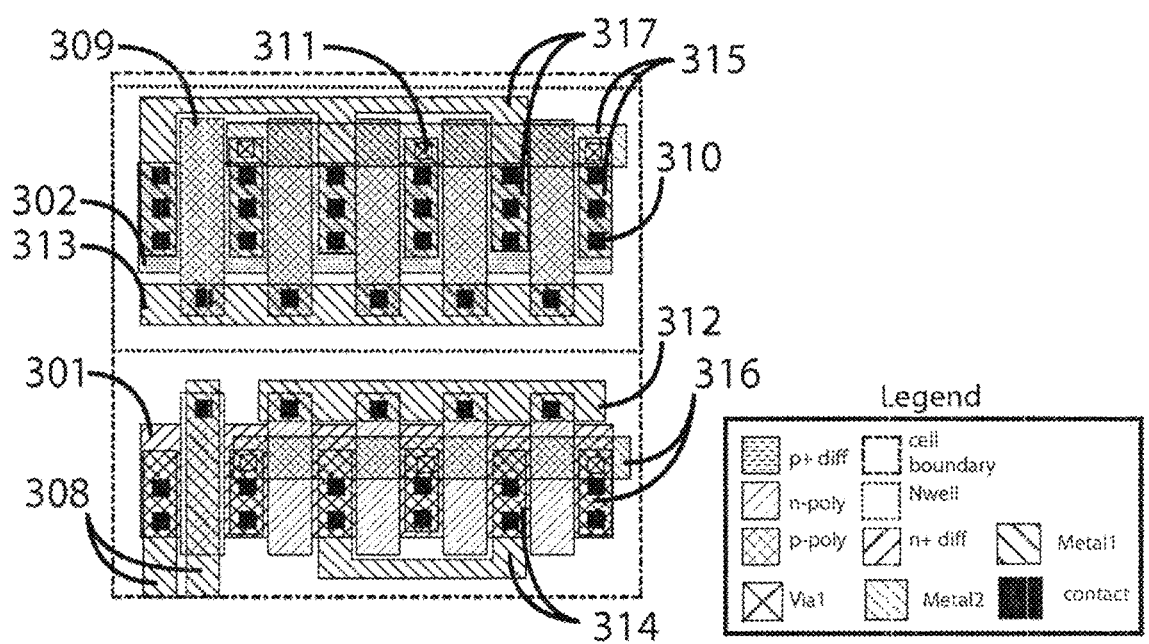
FIG. 5b shows an exemplary layout-level analog standard cell of that exemplary general type analog standard cell after metallization according to one embodiment.

FIG. 5b shows one specific, fully implemented example of the exemplary 5-NMOS-finger and 5-PMOS-finger general type analog standard cell after metallization. This cell is configured with a 4-width NMOS transistor and a 5-width PMOS transistor ('4 and 5'), again in arbitrary units. The PMOS transistor is implemented with a PMOS gate 313 of 5 PMOS fingers 309 that are joined through a plurality of contacts 310 to an arbitrary metal layer 318, a PMOS drain 317 formed by joining 3 of the 6 p-type diffusions 302 through a plurality of contacts 310 to an arbitrary metal layer 318, and a PMOS source 315 formed by joining the remaining 3 unconnected p-type diffusions 302 through a plurality of contacts 310 and vias 311 to an arbitrary metal layer 318. Similarly, the NMOS transistor is implemented with an NMOS gate 312 of 4 NMOS fingers 308 that are joined through a plurality of contacts 310 to an arbitrary metal layer 318, an NMOS source 314 formed by joining 2 of the 6 n-type diffusions 301 through a plurality of contacts 310 to an arbitrary metal layer 318, and an NMOS drain 316 formed by joining 3 of the remaining 4 unconnected n-type diffusions 301 through a plurality of contacts 310 and vias 311 to an arbitrary metal layer 318. The unused NMOS finger 308 and unused n-type diffusion 301 are each joined to additional an arbitrary metal layers 318 through one or more contacts 310 so that they may be connected to the VSS power rail 104 during power and ground routing of the SoC. In each figure description in which one or more arbitrary metal layers are referenced, the use of the same feature number designation in the corresponding figure does not imply any electrical connection between those referenced arbitrary metal layer regions. Furthermore, different arbitrary metal layers may correspond to the same or different fabricated metal layers in an SoC.

The dimensions of the various elements of the general cell 300 of FIG. 5b are drawn as example only and are not intended to restrict the scope of the present invention. Specifically, PMOS fingers 309 need not be of equal length or width to other NMOS fingers 308 or to the PMOS fingers 309, PMOS fingers 309 need not be of equal length or width to other PMOS fingers 309 or to the NMOS fingers 308, p-type diffusions 302 need not be of equal length or width to other p-type diffusions 302 or to the n-type diffusions 301, and n-type diffusions 301 need not be of equal length or width to other n-type diffusions 301 or to the p-type diffusions 302. Furthermore, the number and locations of contacts 310 and vias 311 may be varied. Finally, the specific types of interconnects need not be the same as those suggested by the legends of FIG. 5a and FIG. 5b. Any other variations in layout, features, quantities, or geometries not mentioned also fall within the scope of the general cell 300.

The general cell 300 as just described can have at most one NMOS transistor and at most one PMOS transistor. However, an exception to this can be achieved using the well-known technique of drain/source sharing that is commonly used to reduce layout area and parasitic capacitance. Drain/source sharing is when the drain node of an NMOS transistor is connected to the source node of a second NMOS transistor, or alternatively when the drain node of a PMOS transistor is connected to the source node of a second PMOS transistor. Drain/source sharing, and thus multiple NMOS or multiple PMOS transistors, may be achieved within a single general cell 300. For example, to achieve two NMOS transistors, consider general cell 300 of N=N1+N2 NMOS fingers 308; a first NMOS transistors could have up to N1 NMOS fingers 308 and a second NMOS transistor could have up to N2 NMOS fingers 308. The first NMOS transistor comprises an adjacent pair of NMOS fingers 308 from the N1 group and the second transistor comprises an adjacent pair of NMOS fingers 308 from the N2 group, where both pairs are adjacent to each other as well. The n-type diffusion 301 in between the first and second pairs of NMOS fingers 308 can now form the shared source/drain—it is the source of the first transistor and the drain of the second transistor. Additional NMOS fingers 308 can be incorporated into each NMOS transistor by continuing the same selection of alternating adjacent pairs of NMOS fingers 308 from the two groups as just described. Connection between the corresponding transistor source and drain may be achieved using some conductive segment, for example metal or poly, thereby completing the source/drain shared transistor pair. The same method applies equally to PMOS transistors.

Furthermore, instead of using a general cell 300 to implement source/drain sharing, a source/drain-shared type analog standard cell may be defined as a special type of analog standard cell, just as a moscap type or varactor type analog standard cell is defined. Such source/drain-shared type analog standard cell would differ from the general cell 300 in that it would only include the diffusion and poly fingers necessary to implement NMOS or PMOS transistors, but not both. In other words, a source/drain-shared type analog standard cell can be considered a subset of a general cell 300, such subset being either the top PMOS portion of the general cell 300 or the bottom NMOS portion of the general cell 300.

FIG. 6a shows a typical analog circuit, an NMOS transistor differential pair, consisting of two NMOS transistors connected in parallel as shown. The general layout-level implementation of such an NMOS differential pair is well known in the art, and will only be described briefly.

FIG. 6b shows an exemplary analog standard cell layout-level implementation of the differential pair of FIG. 6a. Within its cell boundary 419 are shown 2 n-type diffusions 401, 2 NMOS gates 412, n-type poly 403, NMOS sources 414, 2 PMOS sources 415, 2 NMOS drains 416, and 2 PMOS drains 417. An arbitrary first metal layer 418 joins the 4 NMOS fingers 408 of each NMOS gate 412 using a plurality of contacts 410. An arbitrary first metal layer 418 makes contact with the left n-type diffusion 401 through a plurality of contacts 410 to form the left NMOS source 414; an arbitrary first metal layer 418 makes contact with the right n-type diffusion 401 through a plurality of contacts 410 to form the right NMOS source 414. The 2 NMOS sources 414 are joined with an arbitrary first metal layer 418 using a plurality of vias 411. An arbitrary first metal layer 418 makes contact with the left n-type diffusion 401 through a plurality of contacts 410, and that arbitrary first metal layer 418 is joined by another arbitrary second metal layer 420 using a plurality of vias 411, to form the left NMOS drain 416; an arbitrary first metal layer 418 makes contact with the right n-type diffusion 401 through a plurality of contacts 410, and that arbitrary first metal layer 418 is joined by another arbitrary second metal layer 420 using a plurality of vias 411, to form the right NMOS drain 416.

FIG. 7a shows another typical analog circuit, a pass gate, consisting of one NMOS transistor and one PMOS transistor connected in parallel as shown. The general layout-level implementation of such a pass gate is well known in the art, and will only be described briefly. FIG. 7b shows an exemplary analog standard cell layout-level implementation of the passgate cell 500 of FIG. 7a. Within its cell boundary 519 are shown an nwell 506, an n-type diffusion 501, a p-type diffusion 502, an NMOS gate 512, a PMOS gate 513, an NMOS source 514, a PMOS source 515, an NMOS drain 516, and a PMOS drain 517. An arbitrary first metal layer 518 joins the 5 PMOS fingers 509 of the PMOS gate 513 using a plurality of contacts 510; an arbitrary first metal layer 518 joins the 5 NMOS fingers 508 of the NMOS gate 512 using a plurality of contacts 510. An arbitrary first metal layer 518 makes contact with the p-type diffusion 502 through a plurality of contacts 510 to form the PMOS source 515; an arbitrary first metal layer 518 makes contact with the n-type diffusion 501 through a plurality of contacts 510 to form the NMOS source 514. An arbitrary first metal layer 518 makes contact with the p-type diffusion 502 through a plurality of contacts 510 to form the PMOS drain 517; an arbitrary first metal layer 518 makes contact with the n-type diffusion 501 through a plurality of contacts 510 to form the NMOS drain 516. The NMOS source 514 and PMOS drain 517 are joined with an arbitrary second metal layers 520 using a plurality of vias 511; the NMOS drain 516 and PMOS source 515 are joined with an arbitrary second metal layers 520 using a plurality of vias 511.

Figure 8A:
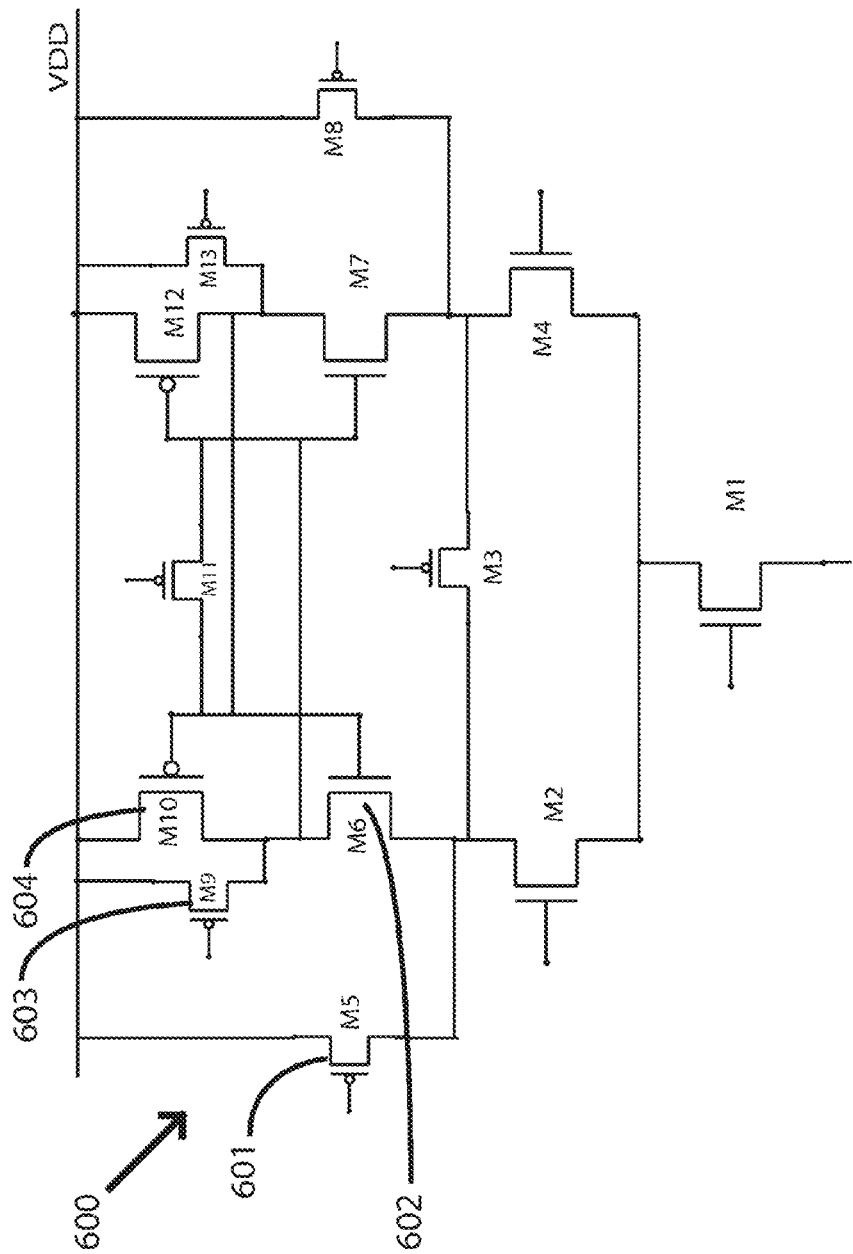
FIG. 8a shows an exemplary transistor-level comparator circuit according to one embodiment t.
Figure 8B:
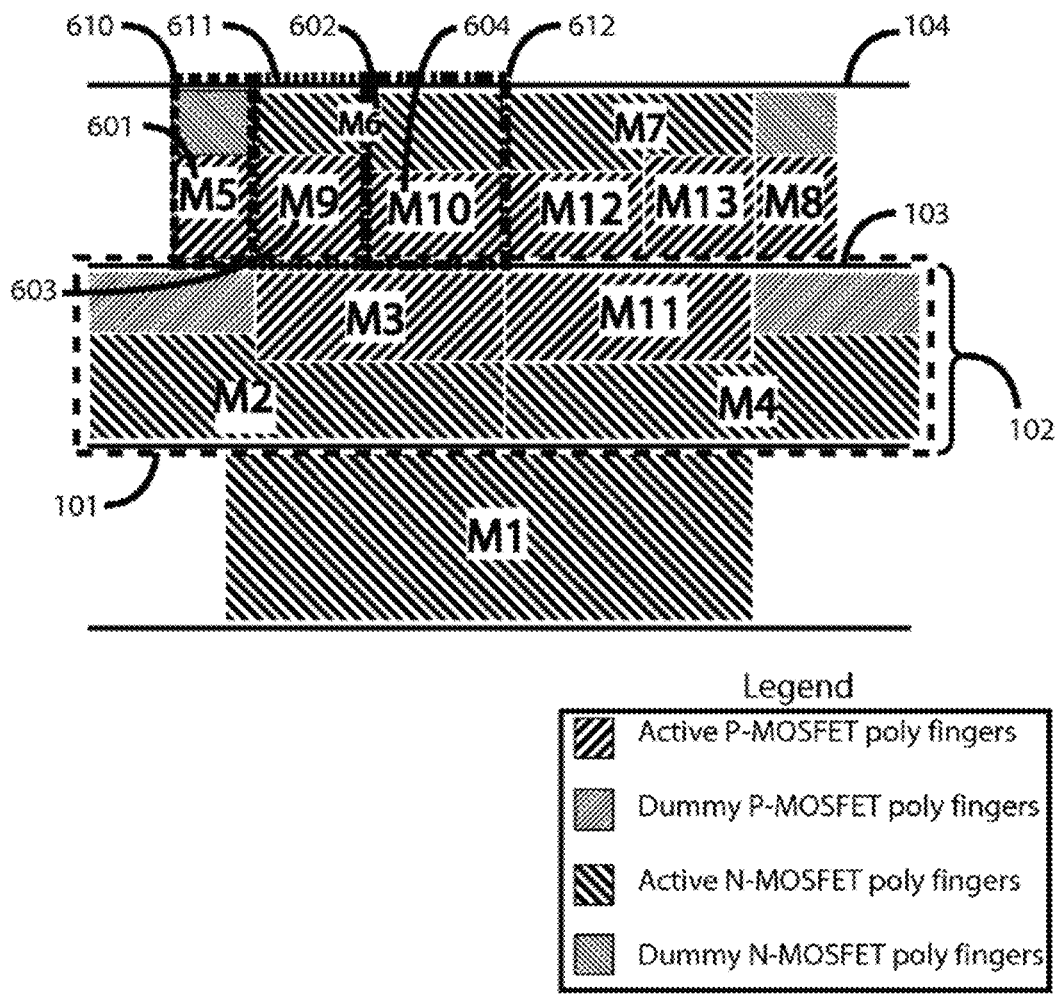
FIG. 8b shows an exemplary mapping and placement of analog standard cells of the comparator circuit according to one embodiment.
Figure 8C:
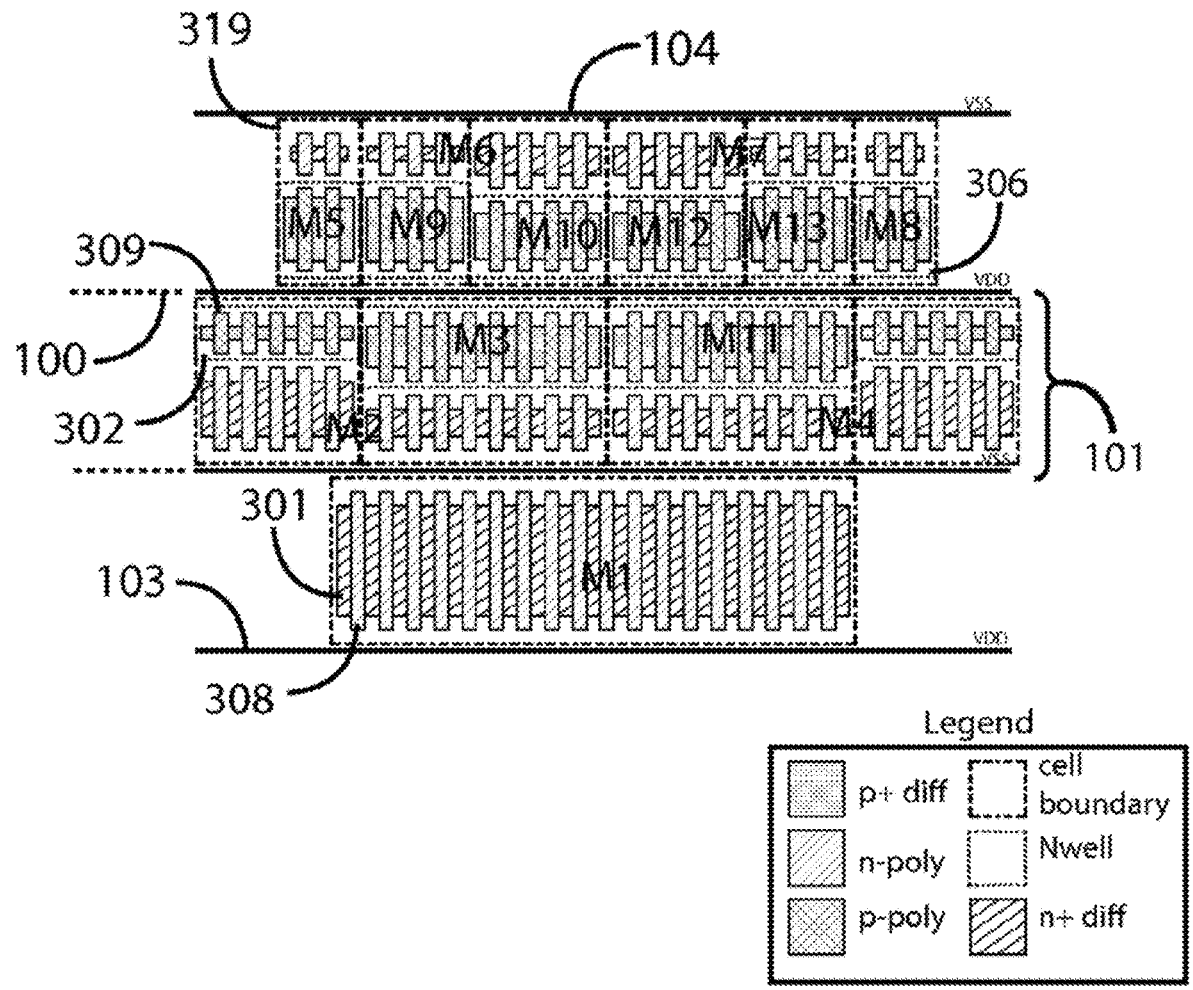
FIG. 8c shows an exemplary detailed view of the mapped and placed comparator circuit according to one embodiment.

FIG. 8a shows a typical analog circuit, a comparator, consisting of a plurality of NMOS transistors and a plurality of PMOS transistors connected as shown. FIG. 8b shows an exemplary mapping and placement of the circuit determined by an ECAD tool. For example, transistor M5 601 has been mapped to analog standard cell 610, part of transistor M6 602 and all of transistor M9 603 have been mapped to analog standard cell 611, and the remainder of transistor M6 602 and all of transistor M10 604 have been mapped to analog standard cell 612. This illustrates the following feature: a single transistor's layout may be achieved by combining multiple analog standard cells. In this example, the layout of transistor M6 602 is achieved by utilizing two general type analog standard cells. FIG. 8c shows an exemplary detailed view of the mapped and placed comparator circuit of FIG. 8b excluding necessary contact, via, and metal layers that would otherwise obscure the layout details that are intended to be the focus of the figure.

Figure 9:
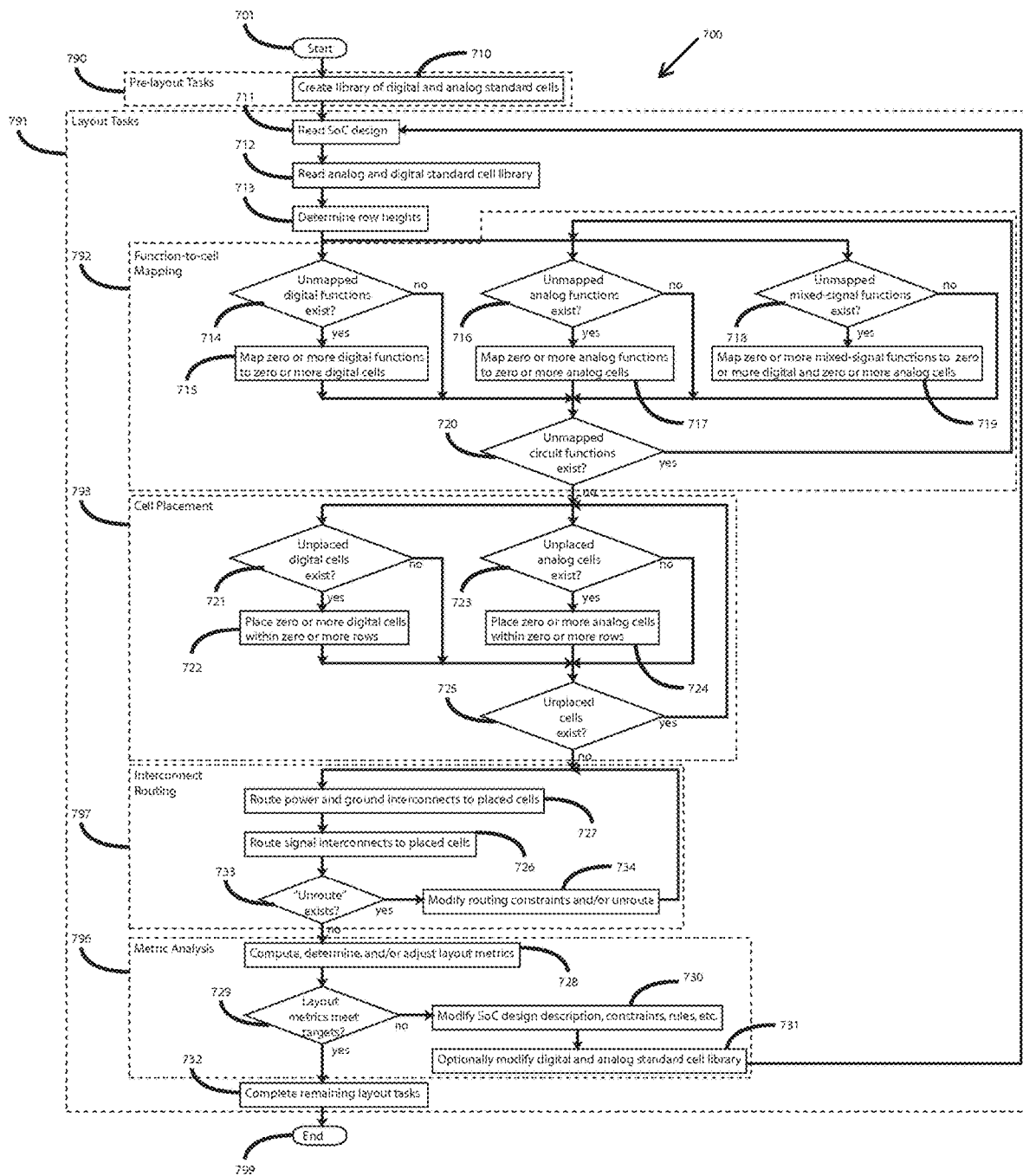
FIG. 9 shows an exemplary ECAD (Electrical Computer Aided Design) physical design flow that utilizes a library of analog standard cells to quickly and efficiently layout the majority of the physical design of an analog or mixed-signal SoC according to one embodiment.

ECAD tools may read, map, place, and route an SoC design to generate the physical layout of an SoC. Analog standard cells may be incorporated into an existing ECAD physical design flow practically seamlessly and transparently, in other words, with relatively simple modification. FIG. 9 shows the process by which a physical design layout may be generated from an SoC design using ECAD tools from start 701 to end 799. Some SoC design is assumed to exist prior to start 701.

Before layout, there may be pre-layout tasks 790. For example, if a suitable standard cell library does not already exists, one must be created, or an existing one must be modified, indicated in create analog standard cell library 710. In a mixed-signal SoC design, the standard cell library should comprise both digital standard cells 201 and analog standard cells 202; in a purely analog SoC design, the standard cell library must comprise analog standard cells 202 and optionally digital standard cells 201.

After pre-layout tasks 790, the SoC design is accessed in read SoC design 711 and the standard cell library is accessed in read standard cell library 712. The SoC design may be in any suitable format, for example a gate-level netlist or a Register Transfer Level (RTL) netlist. Furthermore, this SoC description includes any constraints, annotations, rules, etc. that may be used to aid, guide, or restrict the layout of the circuit, for example timing constraints, transistor drive strengths, or node parasitics.

The row heights 102 are next determined as indicated in determine row heights 713 using any standard conventions in the art. For example, the row heights 102 may be determined by some industry standard, or they may be determined from analysis of the standard cell library.

Once row heights 102 are determined, the SoC design circuits are mapped to digital standard cells 201 and analog standard cells 202. In one embodiment, a function could be used generally to describe circuitry of the SoC design. For example, a digital function could describe some digital circuitry, and an analog function could describe some analog circuitry. The flowchart shows a query made in unmapped digital functions 714, which determines if there is any unmapped digital circuitry in the SoC design. If yes, then zero or more of these digital functions (digital circuitry) are mapped to digital standard cells 201 in map digital functions 715. Similarly, a query is made in unmapped analog functions 716, which determines if there is any unmapped analog circuitry in the SoC design. If yes, then zero or more of these analog functions (analog circuitry) are mapped to analog standard cells 202 in map analog functions 717. Finally, a query is made in unmapped mixed-signal functions 718, which determines if there is any unmapped mixed-signal circuitry in the SoC design. If yes, then zero or more of these mixed-signal functions (mixed-signal circuitry) are mapped to digital standard cells 201 and analog standard cells 202 in map mixed-signal functions 719. The option to map "zero or more" digital, analog, and mixed-signal functions in each of the described flowchart steps is intended to demonstrate that there is no fixed order or procedure of mapping digital, analog, and mixed-signal circuitry to standard cells. The mapping order is arbitrary and more precisely, may be accomplished serially, in parallel, or concurrently. Any suitable convention, algorithm, process, or heuristic may be used to determine the specific map circuit to cells 792 strategy. Finally, a query is made in unmapped functions 720, which determines if there is any unmapped circuitry of any type in the SoC design.

After map circuit to cells 792, the digital standard cells 201 and analog standard cells 202 are placed in rows 101 as indicated in place cells 793. A query is made in unplaced digital cells 721, which determines if there are any unplaced digital standard cells 201. If yes, then zero or more of these digital standard cells 201 are placed in rows 101 in place digital cells 722. A query is made in unplaced analog cells 723, which determines if there are any unplaced analog standard cells 202. If yes, then zero or more of these analog standard cells 202 are placed in rows 101 in place analog cells 724. The placement order is arbitrary, and more precisely, may be accomplished serially, in parallel, or concurrently. Any suitable convention, algorithm, process, or heuristic may be used to determine the specific place cells 793 strategy. Finally, a query is made in unplaced cells 725, which determines if there are any unplaced standard cells of any type.

Once place cells 793 is complete, route interconnects 797 is performed, which includes route power and ground 795 and route signals 794. Although the flowchart shows route power and ground 727 and route signals 726 in that order as is convention in the art, the order is arbitrary, and may be performed serially, in parallel, or concurrently according to any suitable convention, algorithm, process, or heuristic. If the ECAD tool is unable to route all signal, power, and ground lines of the SoC physical design, than an "unroute" failure has occurred, as it is known in the art, as indicated in "unroute" exists 733. If such failure occurs, then the routing constraints may be modified and/or some existing routed interconnects are unrouted, as indicated in modify constraints or "unroute" 734, and another attempt is made to route the interconnects of the SoC physical design.

An SoC design may specify constraints to be met by the layout (physical design), for example signal timing or node parasitics. These constraints, referred to generally as metrics, may be determined, analyzed, modified, or evaluated in analyze layout metrics 796 in an effort to optimize the physical design. Metrics may be computed, determined, or adjusted in determine layout metrics 728, after which they may be analyzed in evaluate metrics 729 to decide whether they satisfy some specified targets. If these metrics are satisfactory, based on any suitable convention, algorithm, process, or heuristic, then any remaining tasks to complete the layout may be performed in complete layout tasks 732. Examples of remaining layout tasks include insertion of dummy stripes of different fabrication layers to make the density of each layer fall within the ranges specified by Design Rule Checks (DRCs). If however, these metrics are not satisfactory, then the SoC design description, which includes design constraints, annotations, rules, etc. may be modified in modify SoC design 730. This modify SoC design 730 step may also include unmapping, unplacing, and unrouting any or all previously mapped, placed, and routed portions of the SoC design and associated layout. Optionally, the standard cell library may be modified in optionally modify library 731. Example standard cell library modifications include expanding the library to include more digital standard cells 201 and more analog standard cells 202, redesigning some existing digital standard cells 201 or analog standard cells 202, or even replacing the library with an entirely different library. ECAD design flow is then re-entered at read SoC design 711 as indicated, and the mapping, placement, routing, and analysis may again proceed.

Layout Automation Methodology

The layout automation methodology of the present invention is generally inspired by the digital place-and-route (P&R) methodology. In digital P&R, circuit layouts are composed of standard library cells that perform basic logic functions. These standard cells are placed and routed according to an input Verilog netlist such that the resulting layout performs the expected function while meeting other performance metrics such as timing, power, and area. Decades of work by many entities have gone into the maturation process of this digital P&R methodology.

In general, the present invention discloses a new methodology that leverages much of this digital P&R technology to solve the analog layout problem. The most difficult problem in P&R is in satisfying thousands of Design Rule Constraints (DRC) while meeting connectivity, area efficiency, timing, noise, matching, and electro-migration requirements. Unlike analog P&R methodology, digital P&R simplifies the DRC problem by decoupling DRC requirements cleanly between cell-level and block-level, and between block-level and chip-level. For digital P&R, a cell can only be placed in predefined standard cell rows. If a cell is DRC clean and the cell pins are placed on the routing grid, then the cell can be easily placed into any cell sites by abutment and routing will generally succeed. Analog P&R allows too much freedom in placement and does not decouple DRC requirements between device-level and cell-level, and between cell-level and block-level. As a result, analog P&R tools are often fragile and difficult to use, and even more importantly, much more expensive to develop than digital because of a lack of regularity, like that of a standardized and fixed row structure in digital. The result is that commercial traction has not been realized, which in turn discourages further investment into analog P&R. This negative spiral feeds on itself to make analog P&R not commercially viable.

One attempt to circumvent the DRC challenge in analog P&R is to directly generate analog/mixed-signal functional blocks, which could be placed and routed more simply, but the shortcoming of this approach was that these functional blocks were often not reusable, as the analog/mixed-signal performance requirements of the same block in different systems were different. By not being able to reuse the functional blocks, the developing of these unique functional blocks became the bottleneck, making the methodology essentially identical to traditional layout methodology.

Another attempt involved building a custom layout optimization tool that can generate analog/mixed-signal layout automatically. The flaw in this approach stemmed from the difficulty in encouraging adoption of a new tool. Without wide-scale adoption of the tool, debugging and support of the tool was challenging, and high tool cost was necessary to offset high development costs of such a custom tool. The present invention's automated layout methodology with Stem Cells avoids these pitfalls by choosing the correct granularity of fundamental building block elements—simple circuit elements, as opposed to analog functional blocks—and by leveraging digital P&R tools, which have a very large installed user base and large teams of software engineers that develop and support the tools. While it may seem somewhat counter-intuitive to create much higher productivity by having a much more constrained design system like digital P&R, as compared to the infinitely-flexible analog P&R, in fact such constraints or lack of flexibility is precisely what gave rise to the tremendous success of digital P&R—by working with much simpler and regular structures, digital P&R has enabled unprecedented productivity increase and innovations that have been fueling the explosive growth in complexity of SoC designs and enabled them to follow Moore's law.

One of the benefits of adopting digital P&R methodology for analog/mixed-signal layout is that the layout generated is, by design, most likely free of design rule violations. Whereas traditional analog/mixed-signal layout engineers painstakingly place polygons while trying to avoid design rule violations. Using digital P&R tools, which are aware of placement and routing design rules, enables automatic placement and routing of design-rule compliant layout.

Another benefit is that since the digital P&R methodology can be highly automated, and thus the time spent in layout can be a small fraction of that of traditional, manual layout, where the effort level has been growing rapidly to the point that it now dominates the entire design time budget, especially in the deep submicron technology nodes, where it has become a prominent bottleneck.

An additional benefit is that a mixed signal critical path containing digital cells and analog cells can have these digital cells and analog cells placed next to each other so their critical path can be shortened. Traditional separation of analog blocks placed far away from digital blocks produced longer mixed-signal critical path.

However, in order to enable automatic analog/mixed signal layout using digital P&R tools, a critical element in the methodology needs to be developed specifically for analog/mixed-signal layout. This element is the complement to the digital standard cell library for analog/mixed-signal circuits. The present invention discloses such cell libraries, called stem Cell™ libraries, to be used as analog elements in the digital P&R flow. The distinguishing characteristics of stem cell libraries will be discussed in more detail in the following sections, but at a minimum, the stem cell libraries must conform to the necessary characteristics found in digital standard cell libraries that allow them to be used in digital P&R tools. Two examples of such characteristics are that the cell heights must be such that they are integer multiples of minimum row heights, and that the cells do not violate design rules when placed together, or abutting, with other cells.

Figure 10:
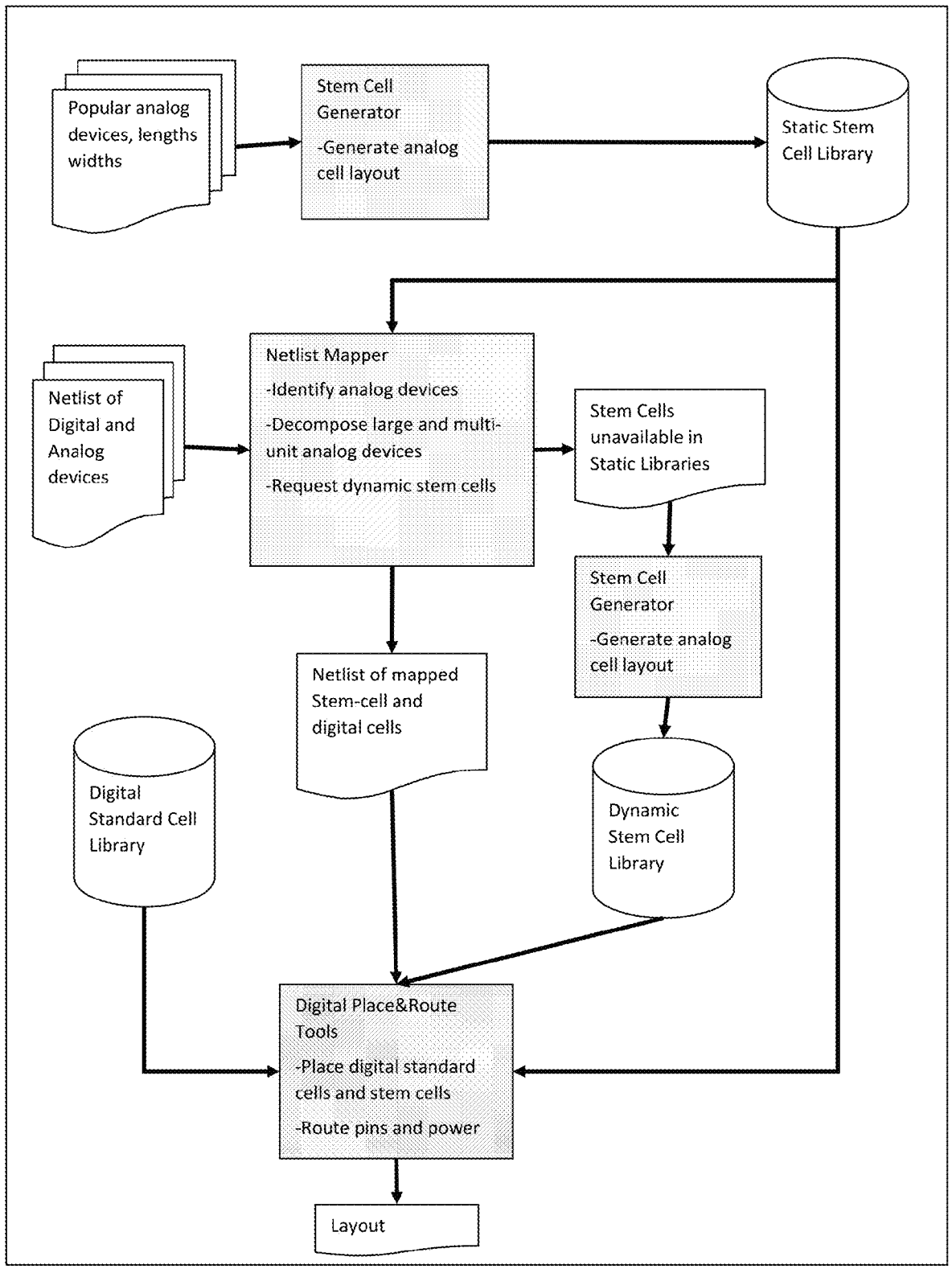
FIG. 10 shows an exemplary flow diagram according to one embodiment.

FIG. 9 shows an exemplary ECAD (Electrical Computer Aided Design) physical design flow that utilizes a library of analog standard cells to quickly and efficiently layout the majority of the physical design of an analog or mixed-signal SoC according to one embodiment. FIG. 10 shows an exemplary flow diagram according to one embodiment.

Stem Cells

The foundation for generating analog/mixed-signal layout using digital P&R tools is Stem Cells. Stem cells are the basic building blocks from which any analog/mixed-signal layout can be generated. Stem Cells are physically identical to digital standard cells from the perspective of digital P&R tools in that the tools can place the Stem Cells based on the geometrical and pin information contained in the stem cell library LEF (Library Exchange Format) file, and generate the layout based on the stem cell layout GDS.

The anatomy of a stem cell layout consists of a core area where the actual device resides, and a framing area that allows the cell to be abutted to other cells while conforming to design rules. The core area is where the device element, be it a transistor, resistor, capacitor, or any other basic device that exists in the device library for that technology, is formed. Various sizes of each device type are placed in the core area to generate different-sized cells. The framing area consists of a ring of alternating minimum sized gate-type material and diffusion-type material. Underneath the framing area are n-type and p-type substrate materials, where half of each cell row is n-type, the other half p-type. Along with the substrate material, there are power rail metals at the top and bottom of each cell row, where the rail over p-type will be connected to ground, and the rail over n-type will be connected to the power supply. All this implies that for a certain transistor instance, half of the area is wasted, as an n-type transistor cannot use the n-type substrate area, and a p-type transistor cannot use the p-type substrate area. This area inefficiency can be somewhat improved by some variations discussed in the following sections. These basic characteristics apply both to older planar CMOS technologies, as well as to more recent FinFET technologies.

Variations from this basic stem cell anatomy can sometimes be useful in increasing overall area efficiency. One example is when the Stem Cells are offset vertically by half a row. This places this single row cell completely within a p-type or an n-type region, thus eliminating the wasted half-row of the "other" substrate type, as mentioned above. Also, within the core area of the device, the substrate/well area shape can be changed such that the ratio between p-type and n-type substrates can be changed. This also leads to increased area efficiency for that certain device. Another variation would be to use Stem Cells that are half-row-height tall, as that could also increase area efficiency by minimizing instantiation of wasteful devices of the opposite type. Another variation is to decrease routing congestion while minimizing routing parasitics for certain cell instances can be achieved through the use of overlay cells that directly connect some stem cell pins to one or both of the power/ground rails. By laying these overlay cells that only contain some metal stubs on top of regular device Stem Cells, power/ground connections can be formed at the lower metal levels, saving routing room at higher layers, thus reducing congestion.

Also, as the power/ground rails are low impedance, direct, short connections to the rails are low-parasitic connections, which are highly desirable. Finally, one additional variation is to remove pin shapes that can be internally routed so that layout area is not wasted by these pins. For example, if the mosfet source is connected to ground, then pin shape for the source and routing from the pin shape to the source is not needed in the mosfet cell and area can be saved. Note that removing pin shapes from the mosfet cell is more optimal than using overlay cells to route the source pin to ground since the pin shape is not generated. Similarly, if the mosfet drain and gate are connected, then more optimal mosfet cell layout can be generated by removing the drain or gate pins.

A collection of these Stem Cells, including the variations and overlay options mentioned above, form a stem cell library, which would then allow the designer to use them in a digital P&R tool to create analog/mixed-signal layout. Each stem cell could be 100% inter-operable with digital cells of the same row row-height and abutment style, e.g. a NAND gate can be placed right next to any stem without incurring any DRC error. In other words, the digital P&R tools will not be able to distinguish Stem Cells from digital library cells. This enables cell-level fine-grain inter-diffusion or intermixing of analog and digital functions seamlessly. However, this comes with a price—there needs to be a different stem cell library for each process technology, much like digital standard cell libraries. Generating many stem cell libraries is quite complex and both time and labor intensive, so automation of this process has been pursued, and the approach taken is discussed below.

Abutment Boundary

In one embodiment, the present invention includes inventive abutment boundary techniques for placing and intermingling Stem Cells with Digital Standard Cells efficiently. Stem Cells are devices or macro layouts that contain a core area that implements the analog or mixed-signal functions and an outer abutment boundary that allows any Stem Cells in the same voltage domain to be placed next to digital standard cells or to other Stem Cells. The abutment boundaries are the left, right, bottom, and top sides of the stem cell layout. The abutment boundary can be empty spaces or fill patterns that allow cells in same voltage domain to abut together in DRC-legal ways.

Figure 18:
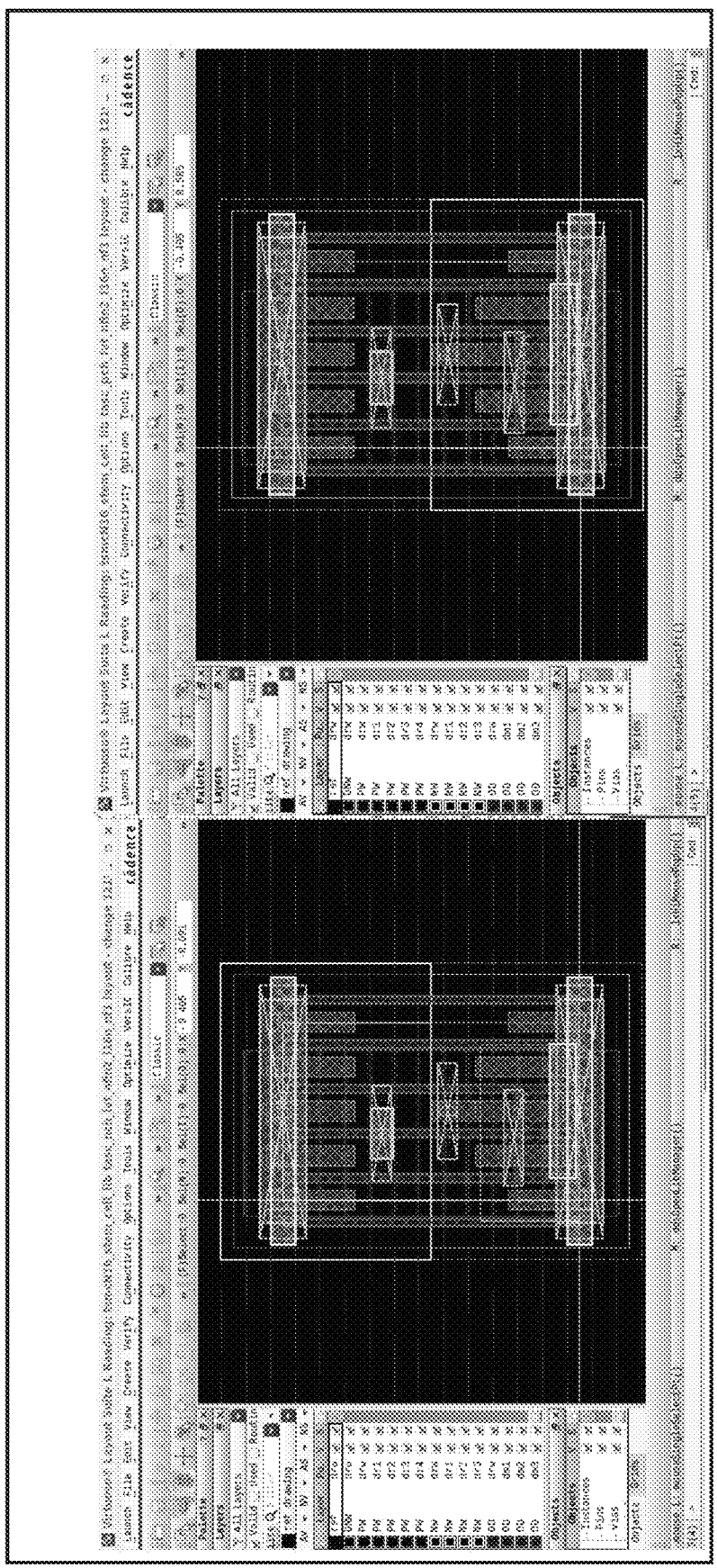
FIG. 18 shows two exemplary standalone Stem Cells according to one embodiment.
Figure 19:
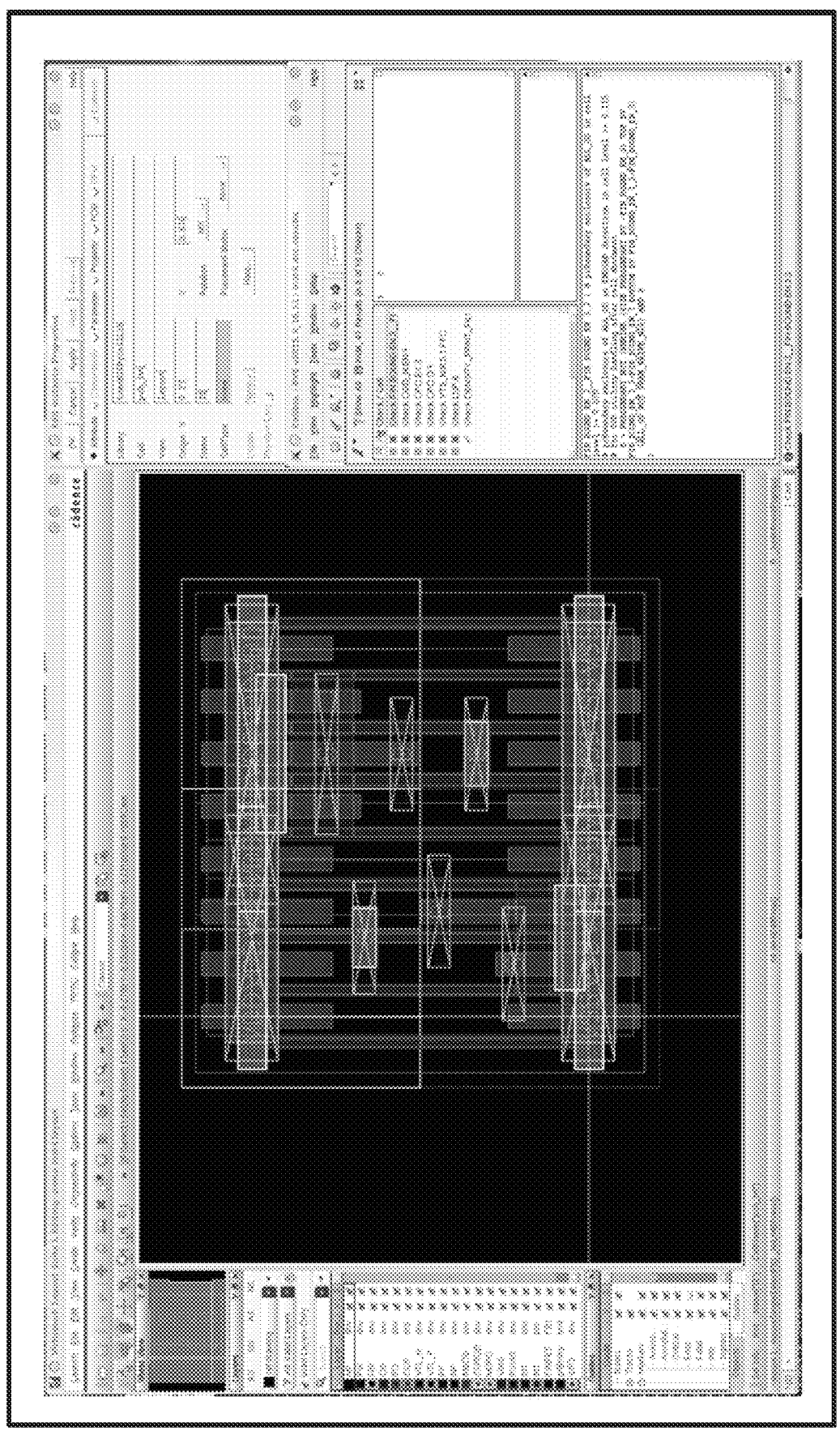
FIG. 19 shows two abutted Stem Cells according to one embodiment.

The following figures illustrate exemplary Stem Cells containing a core analog area and an abutment boundary. FIG. 18 shows a standalone nch_lvt Stem Cell on the left and pcl_lvt stem cell on the right. FIG. 19 shows abutted nch_lvt and pch_lvt Stem Cells.

Figure 20:
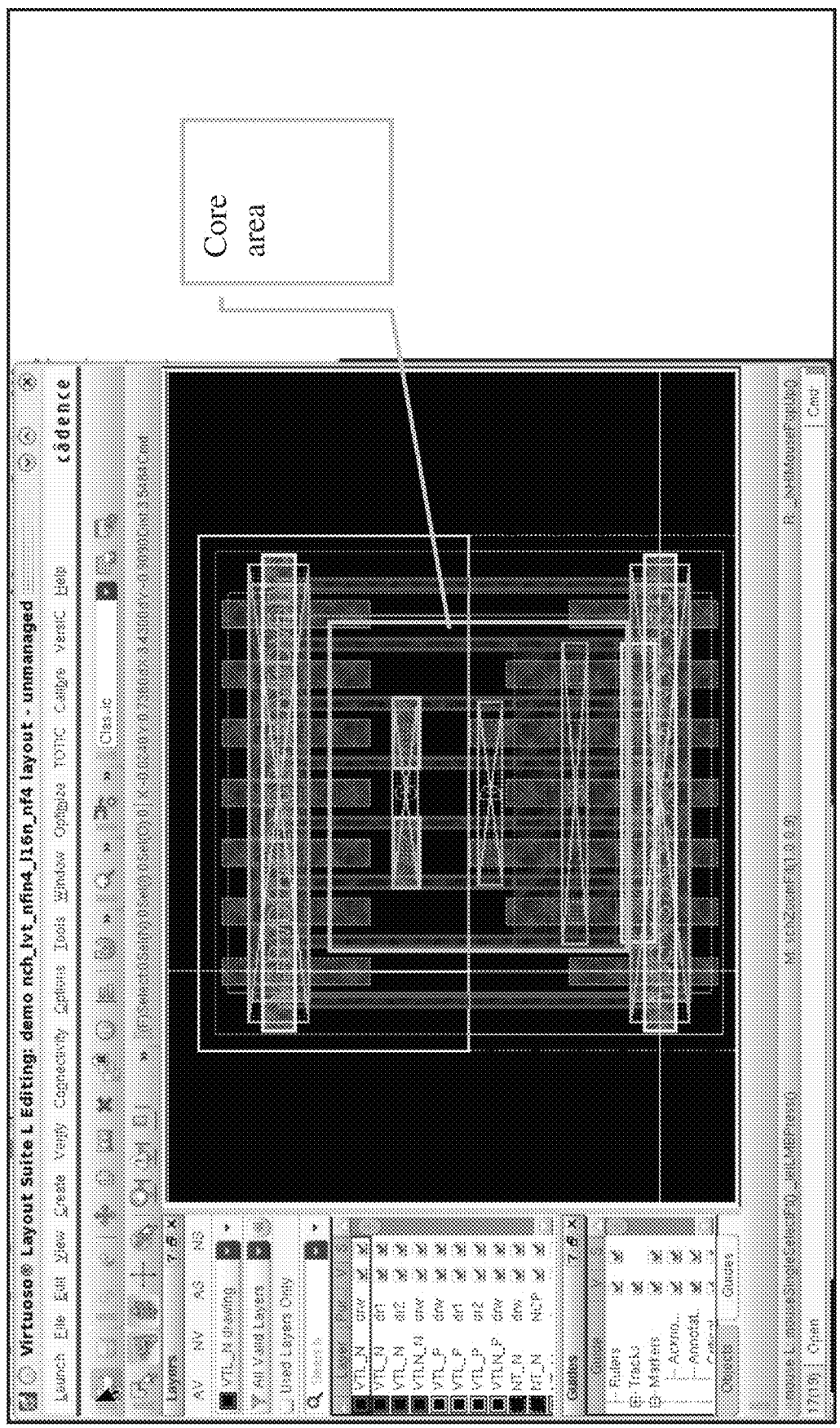
FIG. 20 shows the core area and abutment boundary of an exemplary Stem Cell according to one embodiment.
Figure 21:
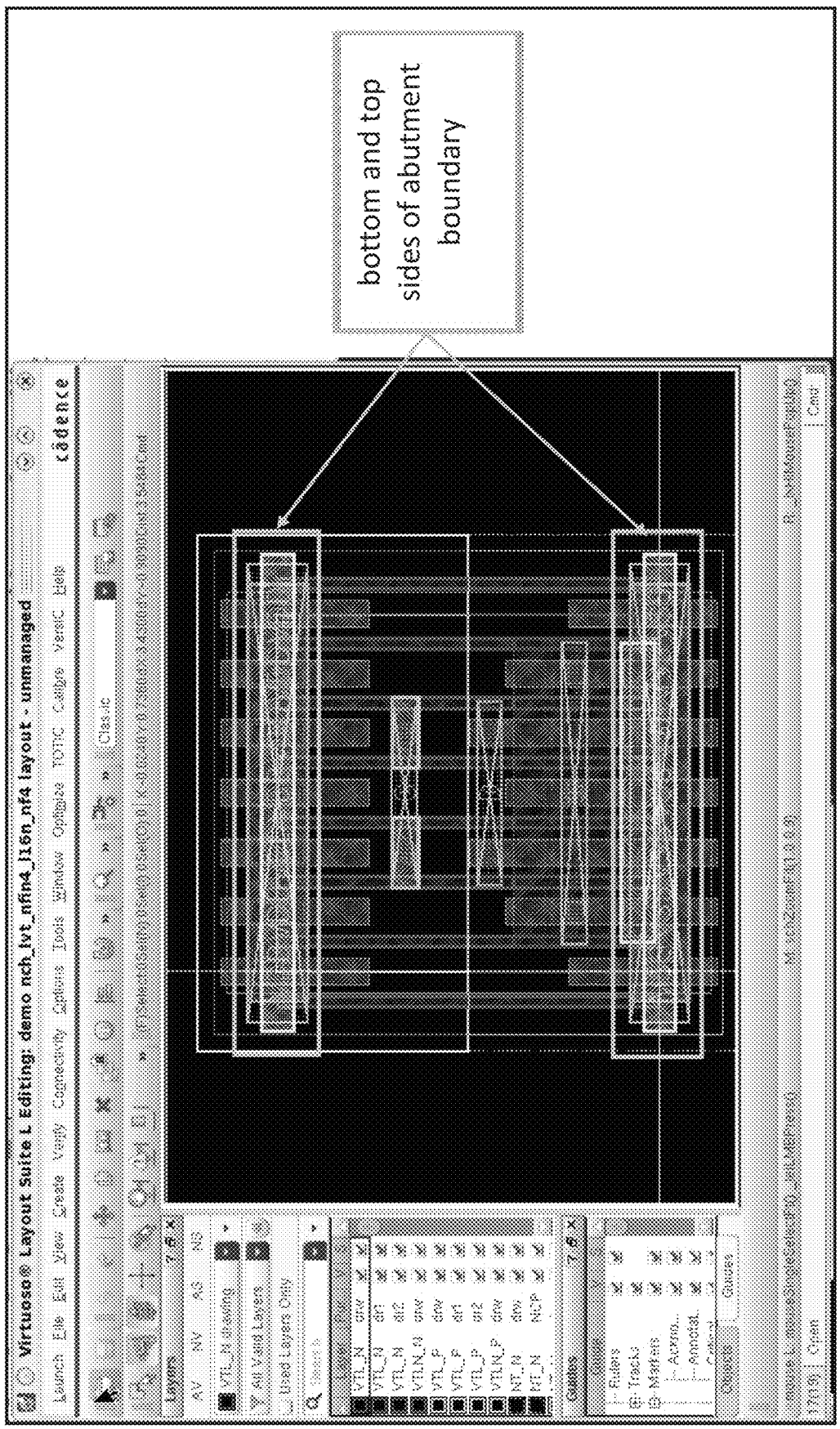
FIG. 21 shows the top and bottom sides of the abutment boundary of the exemplary Stem Cell shown in FIG. 20 according to one embodiment.
Figure 22:
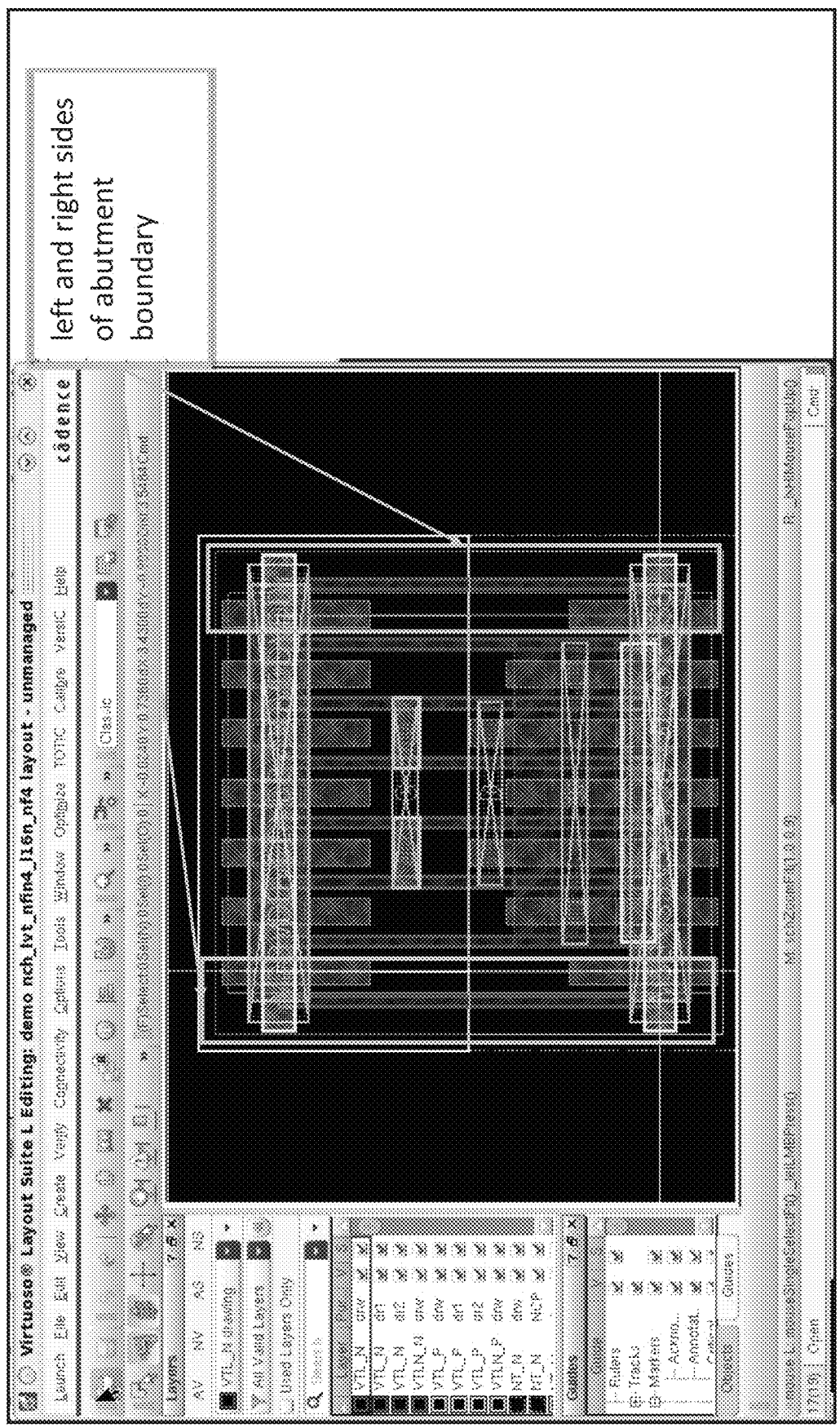
FIG. 22 shows the left and right sides of the abutment boundary of the exemplary Stem Cell illustrated in FIGS. 20 and 21 according to one embodiment.

In one embodiment, the present invention includes specialized abutment boundary that is designed specifically for each class of stem cells, process node, foundry design rules, and voltage-domain application. FIG. 20 shows the core area and abutment boundary of an exemplary Stem Cell. FIG. 21 illustrates the top and bottom sides of the abutment boundary of the exemplary Stem Cell shown in FIG. 20. FIG. 22 shows the left and right sides of the abutment boundary of the exemplary Stem Cell illustrated in FIGS. 20 and 21.

Figure 23:
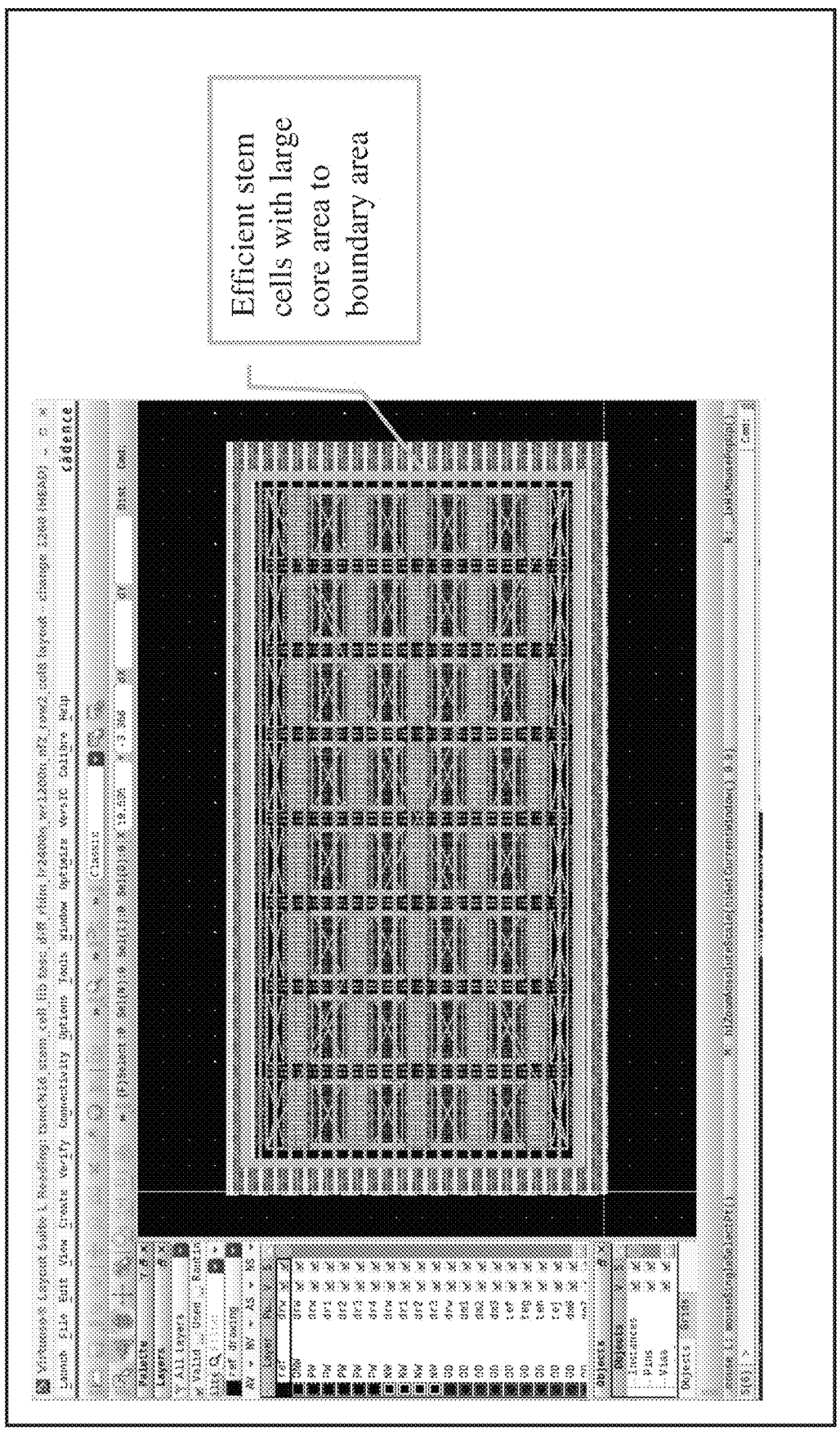
FIG. 23 shows an exemplary efficient stem cell with a large core to boundary according to one embodiment.

In one embodiment, exemplary efficient Stem Cells will generally have large core area to boundary area ratio. These exemplary efficient Stem Cells could be created from unit devices arranged in array or row and column structures. FIG. 23 shows an exemplary efficient stem cell with large core to boundary. As shown in FIG. 23, the core implements an array of diff-pair resistors.

Figure 24:
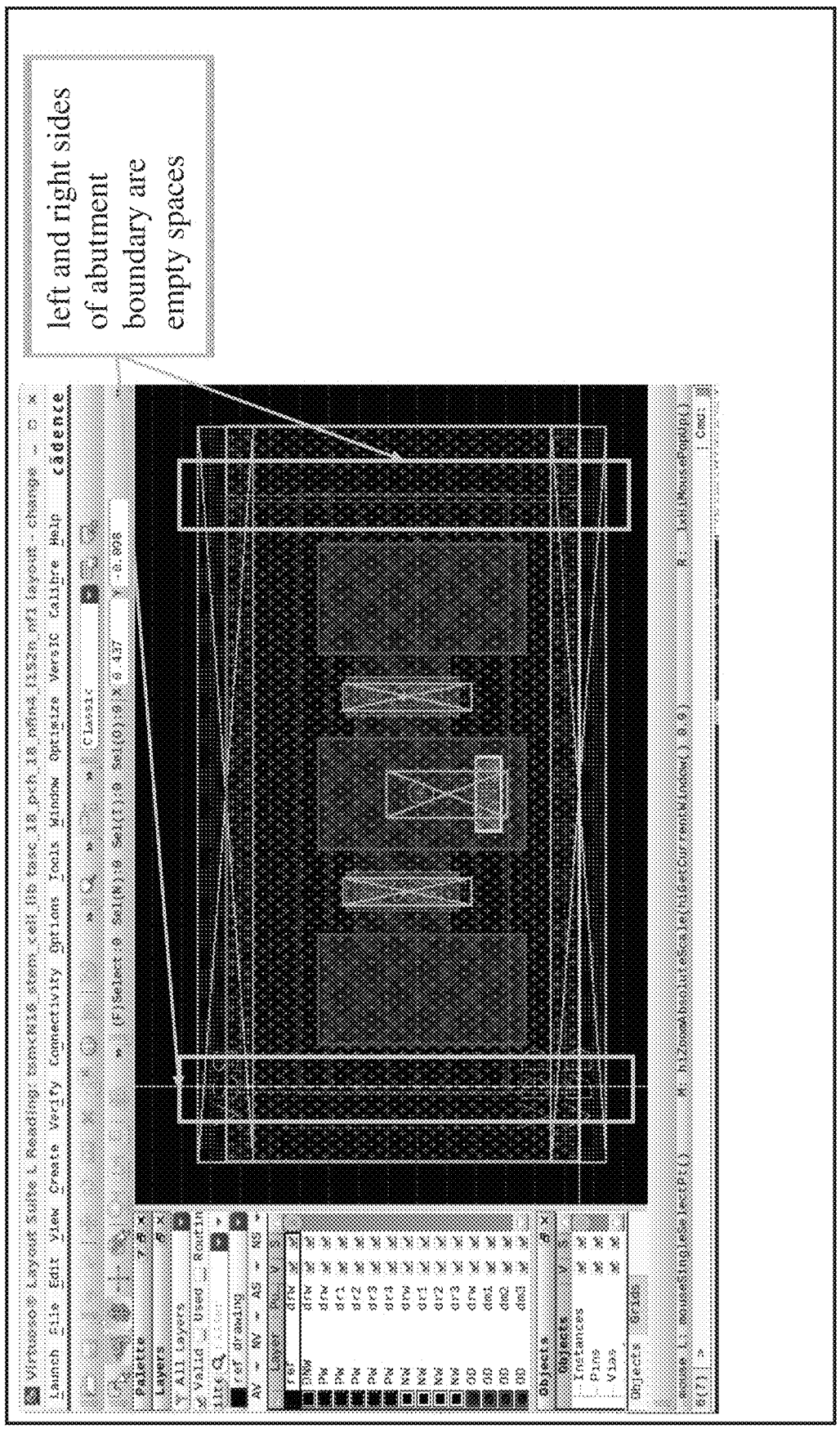
FIG. 24 shows empty area is used for abutment boundary of an exemplary IO Mosfet according to one embodiment.

In one embodiment, the abutment boundary can contain fill shapes as illustrated in FIG. 18 or just empty spaces as illustrated in FIG. 24 depending on the specific design rules and specific applications such as IO voltage-level Stem Cells. FIG. 24 shows empty area is used for abutment boundary of an exemplary IO Mosfet.

Figure 25:
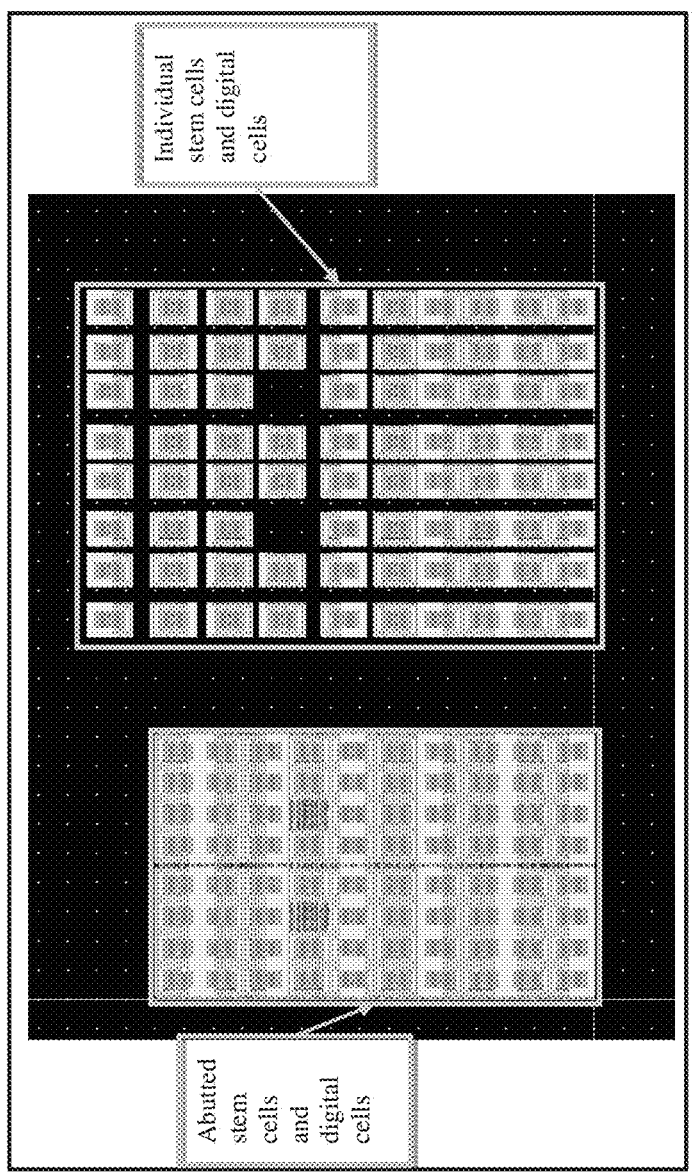
FIG. 25 shows an arbitrary large and complex layout constructed from abutment of exemplary Stem Cells and digital cells according to one embodiment.

In general, Stem Cells' ability to abut to each other and to digital cells allow construction of arbitrary complex layout easily as illustrated in FIG. 25. FIG. 25 shows an arbitrary large and complex layout constructed from abutment of exemplary Stem Cells and digital cells according to one embodiment.

In summary, Stem Cells can be generated manually by hand-drawn or automatically by Stem Cell Software Generator. In one embodiment, Stem Cells can be generated by embedding analog device layout within left, right, top, and bottom boundary fillers. The analog devices can be at the center. The boundary fillers would allow analog Stem Cell devices to abut to any other Stem Cells and any digital standard cells and simplify the problem of placement significantly. Furthermore, the left, right, top, bottom boundary filler could simply be empty spaces in some technology as the requirement is simply to provide DRC legal abutment which empty spaces can satisfy this purpose. In addition, to improve area utilization and reducing loss due to boundary fillers, multiple analog devices can be grouped together as an array at the center. As more analog devices are grouped together, the boundary fillers become an insignificant area overhead. Boundary filler could also provide a well-guarded ring for analog devices so their area in the Stem Cell is not wasted.

Stem Cell Library Generator (Shown in FIG. 10)

Since good Stem Cells are paramount to the present inventive layout automation, much effort has been devoted to automating stem cell library generation. Two reasons to automate Stem Cell generation—1) it is not possible to manually cover the whole space of possible geometries for all devices, and 2) manual stem cell layout generation, which includes correcting DRC errors one at a time is too time consuming.

Stem Cell Generators are generally specialized programmable cell generators that generate different classes of analog devices—mosfet, capacitor, resistor, etc. that meet digital standard cell layout constraints for 1) gridded row height (Cell height must be in multiple of unit row height, 2) gridded cell-width (Cell width must be in multiple of unit cell width), 3) boundary interface shapes and filler allowing both horizontal and vertical abutment to any cell's boundary to be legal, and 4) pin design, which must satisfy minimum area rule and be centered on digital routing grid lines so the digital router can complete connection to pin cleanly.

Digital standard cells have much fewer size variations so they can be hand-created. Analog standard cells have too many size variations and no one had conceptualized a hand-crafted analog standard cell library. The present invention builds analog standard cell libraries (stem cell libraries) and software generators for such libraries.

The choice of creating Stem Cells with digital standard cell compliance simplifies the DRC problem significantly for P&R of analog cells. Without the simplification for digital standard cell compliance, DRC problems in analog P&R will be an order of magnitude more complex, thus making automated analog P&R impossible to achieve.

In one embodiment, besides the distinguishing feature that the stem cell generator can create analog cells that are compliant to digital standard cells rules, additional innovations are necessary to make the stem cell library generator cost effective and production worthy, such as using expert system techniques, hierarchical reusable construction, simplified and reusable design rule abstraction, and portable technology abstraction. The following expands on each of these ideas:

1. Object Oriented Design Technique—The stem cell generator will create specialized classes of mosfets, capacitors, resistors, left, right, bottom, and top boundary fillers, specialized layer contacts and vias. Object oriented design technique improves reusability and is important in allowing the inference engine of an expert system to apply specialized design rule checks for two layout objects using their classes such as contact or rectangle, their function such as gate contact or drain-source contact, their net connection such as whether they will be connected to same net or to different nets.

2. Expert System Techniques—Expert system techniques will define patterns, rules and actions for applying specific design rule spacing check or enclosure check between two objects based on their classes and functions. The expert system is the most complex algorithm in the cell generator due to the numerous rules and situations that must be considered. Machine learning techniques will be considered for supplementing the expert system so design rule calculations will be much simpler.

3. Hierarchical Reusable Construction Improves Reusability of Lower-Level Cells—At the bottom level of the reusable cell hierarchy are the Rectangle cell, Instance and Instance Array cells, and Contact cells. At the middle level are the TransistorStack (Mosfet Source, Drain, Channel) and Boundary Filler (poly, m0diff, and well straps) cells. At the top level are the Mosfet, Resistor, and Capacitor.

4. Simplified and Reusable Design Rule Abstraction—Simplified and reusable design rule abstraction is used to simplify rules for the expert system. Advanced technology node contains approximately 10,000 design rule parameters. An expert system supporting all rules would be prohibitively expensive to develop. While simplified and reusable design rule abstraction for the stem cell generator is related to existing digital place and route technique of simplifying design rules, the stem cell generator simplified and reusable design rule abstraction will set pioneering standards in simplifying rules and layers not supported by digital place and route. Simplified rules for poly layer, diffusion layer, and contact-less metals will be newly developed techniques to make cell generator easier to implement. Foundry design-rule manuals don't abstract similar rules leading to numerous rule parameters. Careful mapping from complex foundry rules to simplified stem cell generator rules will allow easier expert system programming and generation of DRC correct cell layout. There will be two distinguish set of stem cell library design rules.

a. Technology design rules are those rules imposed by the foundry manufacturing process b. Standard cell library design rules are those rules imposed by the standard cell library selection of row height, number of routing tracks, and power fabric width. It is possible to have different stem cell libraries depending on different choices of standard cell library design rules. A software cell generator is important for generating different stem cell libraries for different standard cell library design rules efficiently.

5. Portable Technology Abstraction—Portable technology abstraction is necessary to port among different foundries such as TSMC and GLOBALFOUNDRIES. The stem cell generator will use an abstract technology and map abstract layers to foundry specific layers, and abstract rules to foundry specific rules. While it is easy to map an abstract layer such as stem cell diffusion layer to TSMC OD layer because such mapping is one-to-one, the mapping of abstract stem cell design rule to specific foundry design rule is more complex since the mapping of design rules will not be one-to-one.

The Stem Cell Netlist Mapper, discussed below, and the Stem Cell Generator are fundamental to completely automating or drastically reducing mixed-signal layout effort since all 3 steps of cell generation, placement, and routing will be automated by software as shown in FIG. 10.

The Stem Cell Library, disclosed in the present invention, is generally an extension of the ASIC standard cell library concept, and it has two library types: 1) a static cell library type, and 2) a dynamically-generated cell library type.

Similar to a digital standard cell library, Stem Cells with frequently-used lengths and widths can be created for use by many designs without knowing each design ahead of time. These stem cell libraries are called Static Stem-Cell Libraries. They can be created ahead of time to save runtime incurred by dynamic cell generation during layout synthesis. This static library also contains smaller stem-cells (as compared to the dynamic library) that are conducive to gap-filling by restricting the cell aspect ratio. The general purpose is to get a quick prototype layout that is not yet area optimized. The area-inefficiency is caused by many unnecessary abutments of such smaller fine-grain Stem Cells. The benefits of having this first iteration could include:
1) Quick turnaround;
2) Initial area and critical path length estimates; and/or
3) Clusters formed by the same type of Stem Cells can provide an approximate bounding rectangular outline. This outline is the means for the mapper to replace each irregular cluster with a rectangular array of Stem Cells that are much more area efficient. This necessitates dynamic generation of a rectangular array of the same Stem Cells by the dynamic library generator, which will be described in details below.

Analog cells have too many variations in lengths, widths, fins, number of fingers to be completely represented in a static library. A Static Stem-Cell Library can only store a most-frequently-used subset. Remaining necessary cell sizes for the design that are not part of the static library, can be obtained from the Dynamic Stem-Cell Library.

The inventive Stem Cell Generator can be used to generate cells for both static and dynamic stem-cell libraries. Both static and dynamic stem cell libraries are provided for different customer usage preferences. It is expected users or a synthesis tools will use predominantly static stem-cell libraries and invoke the Stem Cell Generator to create a few design-specific cells that do not exist in the static libraries.

Figure 11:
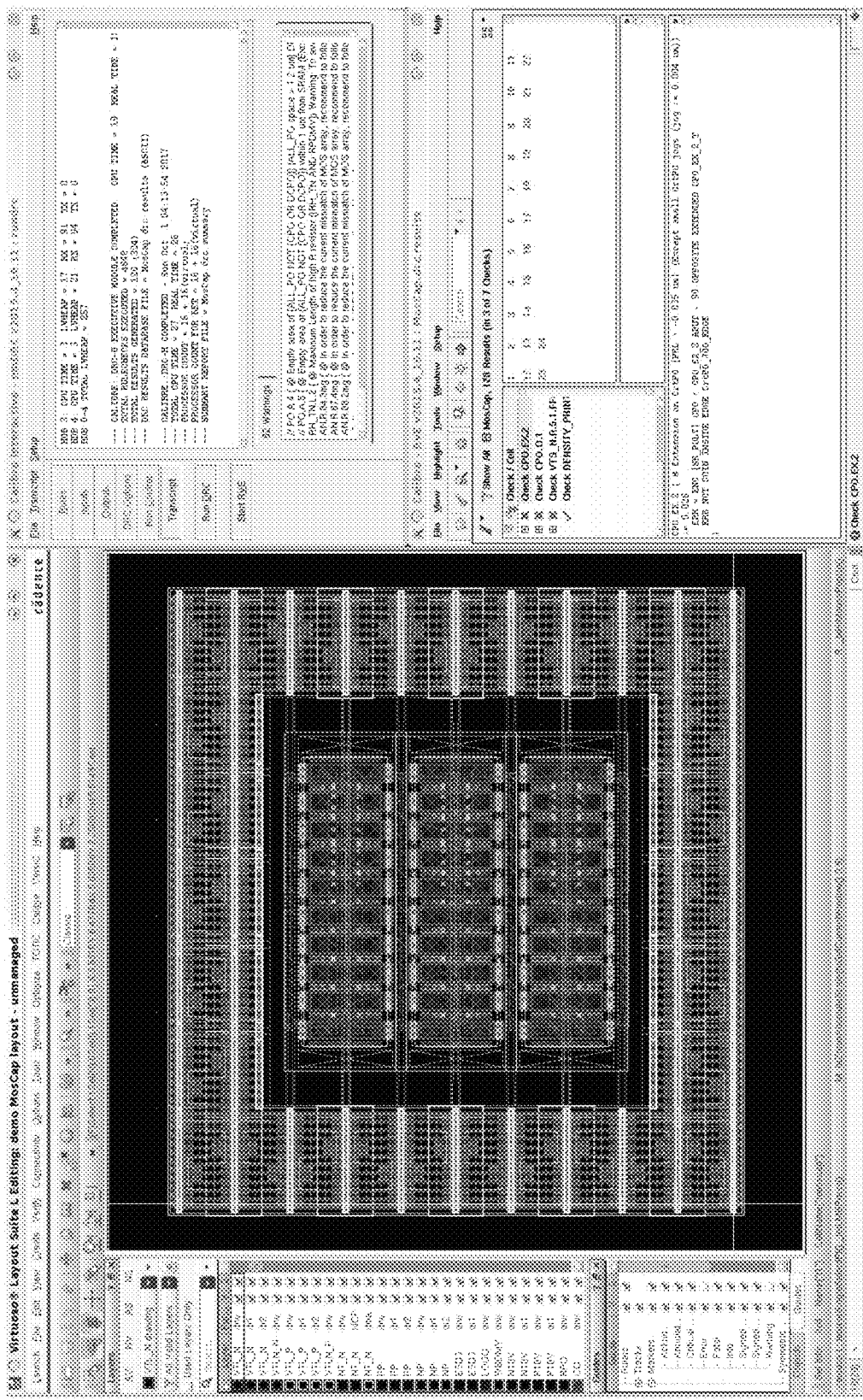
FIG. 11 shows an exemplary DRC (Design Rule Check) and LVS (Layout-Versus-Schematic) clean layout according to one embodiment.

In addition, the dynamic Stem Cells can be used to optimize area and shorten critical paths, as mentioned above. As an example, for an input analog cell layout specification of type=moscap, gateLength=0.18 μm, nrow=3, nfin=16, nf=7, the Stem Cell Generator will produce a DRC and LVS clean layout as shown in FIG. 11.

In one embodiment, the Stem Cell Software Generator can provide parameter options for creating efficient layout. For example, a diode-connected or gate-drain tied mosfet can be routed internally to reduce area and resistance that are caused by separate gate and drain routing. Furthermore, diff-pair structures can be merged into one cell for improved matching and area efficiency. In addition, internal routing wires and pins could be sized by parameters to meet Electromigration and IR drop requirement.

In one embodiment, Stem Cell Software Generator library is designed with reusable hierarchical structures as follows:
a. Bottom-level contact cells, rectangle cells are used to create reusable contacts and rectangle supporting named identification.
b. Mid-level boundary-filler cells, transistor-stack cells use bottom-level contact cells and rectangle cells.
c. Upper-level transistor cell and moscap cell uses mid-level transistor-stack cells and filler cells.
d. Current cell can reuse lower-level cells. Lower-level cells can be referenced by hierarchical names for routing and placement. For example "Imid1/Ilower2/ImplantRect" can be referred from transistor cell to get dimension of implant rect two-level below in the design hierarchy.
e. Current cell can compose lower-level cells by abutment, superimposition, or making array.

Netlist Mapper (as Shown in FIG. 10)

In one embodiment, the inventive layout acceleration methodology focuses on quickly generating layouts from schematics. As such, the schematic design process is identical to traditional design methodology, where circuit designers generate schematics and verify functionality at the schematic level using test benches. The difference from traditional design methodology starts when the circuit schematic is handed off as the input to the inventive methodology. The device elements in the schematic netlist are mapped to appropriate Stem Cells by the netlist mapper.

In general, the netlist mapper is sufficiently intelligent to select the device sizes that are closest to the sizes used in the original design, so as to minimize performance differences between the original schematic and the new netlist. The netlist mapper result can be fed into the original schematic test benches to confirm that the mapping error causes only acceptable changes in performance. The netlist mapper also converts the netlist into Verilog format, as that is the file format required by place and route tools.

In one embodiment, some of the general functions that are encapsulated in the mapper could include:
1. Selecting stem cell device sizes that are closest to the sizes in the original design.
2. Selecting parallel and series decomposition of resistors to meet resistance and current limit in each unit resistor.
3. Selecting nRows*nColumns Array or Matrix Stem-Cell Builder for composing a large device from nRows*nColumns small unit devices. A large device has higher current and EM requirement, digital router may not size up routing wires correctly for the large device that is created from an array of smaller unit device.
4. Selecting more optimal mosfet Stem-Cell for mosfet with grounded sources or mosfet with drain-gate diode connection.
5. Merging some devices when appropriate. For example, a differential pair of transistors can be merged into 1 single special diffpair cell.
6. Identifying different power domains so the place and route tool can partition the design correctly.
7. Delivering the new netlist in Verilog format, which place and route tools recognize.

As stated above, the device elements in the schematic netlist are mapped to appropriate Stem Cells by the netlist mapper, which is a software program that takes in a schematic netlist, and produces stem-cell-mapped Verilog netlists for use in place-and-route tools. The first general step of the netlist mapper involves a schematic preprocessor that sees if some devices can be merged into a bigger device. Devices of the same type, with the same terminal connections, may be merged in this step. This allows the mapping result to consist of fewer elements, leading to smaller layout. However, some designers may prefer not to merge devices for their own reasons such as better matching of transistor performance across the devices. In this case, the merging can be skipped to honor the designer intent.

After the merging step, mapping is done to match as close as possible the important device characteristics, such as device widths and lengths, number of fins, and number of fingers. It is possible for a schematic device to be mapped to multiple smaller Stem Cells, that when combined, would match the characteristics of the original schematic device. As an example of these steps, a circuit designer might instantiate 8 parallel copies of a transistor to drive 8 times as much current as a single transistor. Blind mapping without merging would result in 8 Stem Cells (one stem cell for each copy of the transistor), or some multiple of 8 Stem Cells if each copy of the transistor gets mapped to multiple Stem Cells, but through merging, the 8 parallel transistors could be converted into one transistor that is 8 times larger before mapping. After mapping, this would result in one, if not a few, Stem Cells. Since there is some area overhead associated with each instance of a stem cell, reducing the total number of Stem Cells increases the area efficiency of the overall layout, and improves layout parasitics, as total distance between devices to be connected shrinks.

As for the actual mapping operation, there could be three sequential levels of stem cell mapping as follows:

1) An exact match of schematic device to stem cell devices found in the stem cell library
2) Dynamically generate a stem cell to exactly match the schematic device
3) Map to the closest stem cell device using Stem Cells in the library and via dynamic generation Exact matches via the first 2 options are strongly preferred, as without exact matches, later stages in the methodology such as LVS (layout-versus-schematic) checks, and performance verification may not match the original schematic.

In one embodiment, the present invention includes a fixed-size stem cell library which accounts for the most often used device types and sizes, to balance the need for comprehensive device characteristics against the need for manageable library size. If the library is too small, most devices will have to be generated dynamically, which increases computation time. If the library is too large, the place-and-route tool will slow down in loading the large library. As such there is a balance that needs to be achieved with regards to library size.

With the third mapping option, the mapper is sufficiently intelligent to select the device sizes that are closest to the sizes used in the original design, so as to minimize performance differences between the original schematic and the new netlist. For transistors, the mapper could try to match the active device area (W/L or number of total fins). The transistors in the stem cell library consists of transistors with gate width per finger and number of fins per finger that are neither too long (too many fins) nor too short (too few fins), as either extreme can hamper performance. For resistors, the mapper could try to match the width of the resistor first to meet the designer's intent for EMIR requirements, then try to match the length so that the L/W is as close as possible to the schematic design. For capacitors, the mapper could try to map the total area (W*L) as close as possible to the schematic.

In one embodiment, the netlist mapper could produce a report that indicates the mapping error, or the difference between the schematic parameters and the mapped parameters, to provide some indication of the quality of the mapping. The mapped netlist should also be fed into the original schematic test benches to confirm that the mapping error causes only acceptable changes in performance. Finally, the mapper could generate the netlist in Verilog format, as that is the file format required by place and route tools.

While the above description summarizes the basic functions of the netlist mapper, some additional functions exist to facilitate the downstream place-and-route and performance verification steps, such as:
1) Power domain identification and assignment
2) Conglomeration of devices into macros
3) Current-aware device sizing/selection
4) Mapping to Stem Cells with specialized connections In the first function, power domain identification and assignment, every device is assigned to a power domain by tracing through the schematic connectivity to identify which power supply is connected to that device. This information is necessary during place-and-route to isolate different power domains, which means keeping the power grid and substrate and well voltages separate for different power supplies. Without this, layouts will not pass design rule checks (DRC).

The second function, conglomeration of devices into macros, consists of placing certain devices close together, usually in regularly-structured format, and connecting these devices together. This macro-ization is performed on devices that are critical to performance, and the goal of this operation is to minimize the parasitic resistance and/or capacitance between these devices. The identities of these critical devices are provided to the netlist mapper, which then adds a layer of hierarchy in the netlist to separate out these devices into a module, which will be instantiated in the place-and-route tool as a macro.

The third function, current-aware device sizing/selection, is necessitated by the requirements to keep voltage drop and electromigration under control. While the current flow is determined by the performance requirement and schematic design, using Stem Cells with too-narrow wires can have too much resistance, leading to large voltage drops, and too much electromigration. In order to counter this, Stem Cells with more metal wiring should be used, and the netlist mapper needs to be aware of this. The current flow requirement is provided to the netlist mapper, and the mapper can use that information to select the correct stem cell such that voltage drop and electromigration requirements can be met.

The fourth function, mapping to Stem Cells with specialized connections, uses the connectivity information for a specific device to map to specialized Stem Cells. An example of this is a MOSFET with its source terminal tied to the supply or ground. This is a relatively common connectivity configuration for a MOSFET, and as such, it makes sense to map this device to a specialized stem cell that has this connectivity to the power/ground rail built in. The advantages of this are two-fold: first, the routing parasitics to the supply can be minimized, as a good connection to the supply rail can be made within the stem cell, and second, keeping the supply route within the stem cell eases routing congestion in the higher layers, where the supply routes would have been without the specialized stem cell. Other examples of such Stem Cells with special configurations would be grounded-gate nMOSFETs, and diode-connected (gate tied to drain) MOSFETs.

With the above steps completed, the mapped netlist which consists of Stem Cells and macros, can then be fed into the digital place-and-route tool, along with the secondary information generated by the mapper such as power domain information.

Digital Place and Route Tool

Figure 13A:
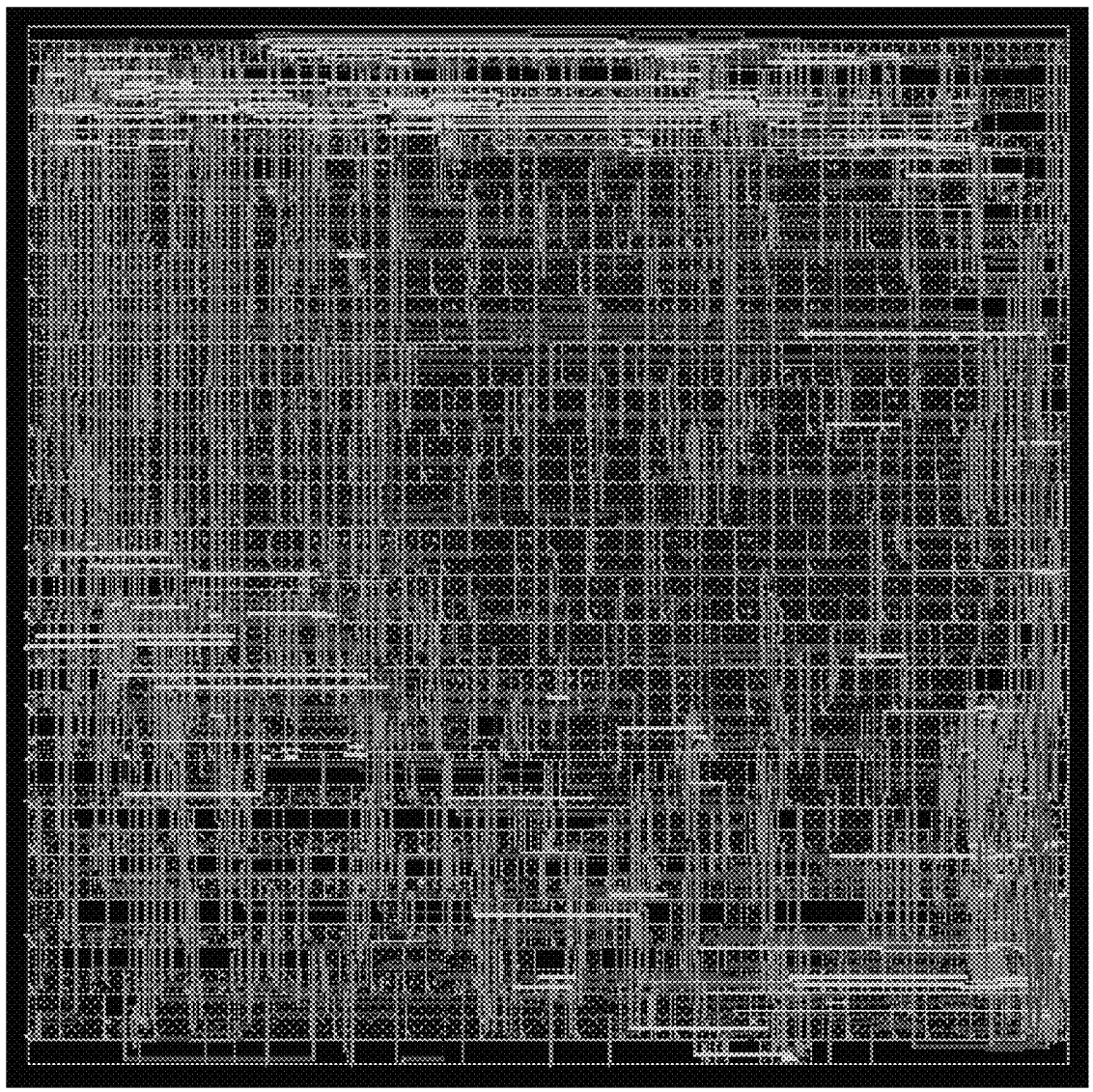
FIG. 13A shows an exemplary a first pass trial layout of CTLE (Continuous Time Linear Equalizer) according to one embodiment.

The place and route tool takes as its input the Verilog netlist from the mapper, stem cell library LEF and GDS, and the technology file. This is the minimum requirement to run the first iteration of place and route, although the result is usually less than satisfactory. An example of a typical first iteration is shown in FIG. 13A, which shows a first pass trial layout of CTLE with the inventive Stem Cells in 28 nm technology with a size of 48 μm×48 μm.

Most often, there are additional pieces of information that can be provided to improve circuit performance. One such piece of information is pin placement. In the case of a subcircuit that is being laid out, there are usually constraints on how that subcircuit connects to the higher-level block, and that is defined in the pin placement. The pin placement then constrains the placement of elements in the sub-block such that the overall routing distances are minimized. Poor pin placement can significantly harm the performance, as in the case where 2 signals are required for some operation, but if they come from opposite ends of the sub-block they may have timing or amplitude problems. This may necessitate modification of the pin placement, which would then impact the higher level placement, as the connections to this sub-block would be different.

Figure 13B:
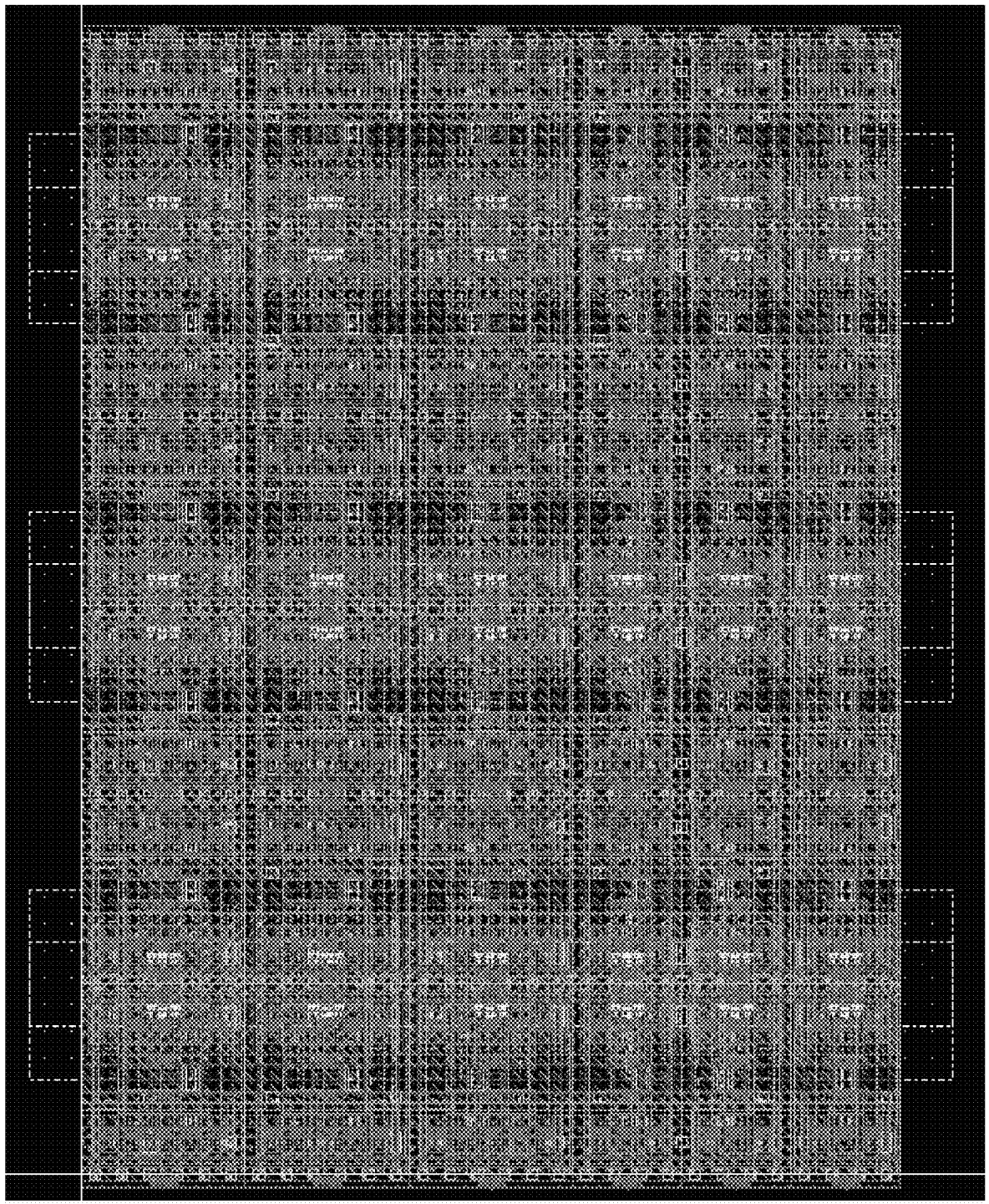
FIG. 13B shows an exemplary macro compiler result according to one embodiment.

After pin placement, another level of optimization that can be done is through placement constraints. By intelligently placing sensitive components, parasitics at the critical nodes can be minimized, resulting in better performing designs. Two methods are available to constrain placements—using a macro compiler, or using dynamic placement constraints. The macro compiler is an inventive tool that takes a portion of the netlist, places the components in that portion in an array, and routes them structurally within the new macro. By imposing a grid structure on these components, parasitics can be minimized. An example of the macro compiler result is shown in FIG. 13B, which shows a Macro generated automatically by the inventive Macro Compiler with regularity of the structures to minimize routing parasitics.

In one embodiment, some of the basic operations of the macro compiler functions can be subsumed by the dynamic stem-cell generator when it is simply a composition of the aforementioned regular array of the same Stem Cells, with certain structural routes overlaid on top. For more sophisticated macros, dynamic placement constraints utilize commands in the place and route tool to either place components at specific coordinates or with some offset with respect to another component. These commands can be used to place specific components next to each other, when adjacency or symmetry needs to be maintained. It should be noted that these placement constraints need only be applied to critical elements, which tend to be a smaller subset of elements.

A final knob for optimization is routing constraints. After placing some elements intelligently, the routing parasitics can be further controlled through some routing directives. The place and route tool tends to select minimum width metal wires to ensure connectivity, but that sometimes is insufficient from a circuit performance perspective. In order to achieve better performance, the first parameter that can be controlled is the wire width. Wire widths can be finely controlled, as they can be specified on a net-by-net basis, as well as a metal-layer-by-metal-layer basis. However, even after increasing wire widths to reduce parasitic resistance, the automatic router sometimes does not achieve the desired routes. In such cases, more manual intervention can be necessary, where any or all of wire width, metal layer, or exact wire coordinates, can be specified for each critical net.

An alternative to manual placement and routing constraints may be to use the internal optimization engine in the place and route tool in an unconventional way to get better performance. The place and route tool contains an internal engine to optimize place and route for digital circuits based on timing information for digital standard cells. This information is usually provided in timing files which contain setup times, hold times, drive strengths, and input loads. The place and route tool uses this information, combined with routing wire parasitic delay, to optimize digital circuit timing. While designed analog circuits designed by the invention methodology may not have concepts of setup time and hold time, a goal of the inventive place and route methodology is the same, in that the routing wire parasitic delay, which is a combination of series resistance and loading capacitance, needs to be minimized. This problem can be further constrained by only applying this optimization to the critical nets where minimizing parasitics is crucial for performance. By providing a variant of these timing files for Stem Cells, layout improvement could be achieved.

Similar to the utilization of timing-driven P&R, the EMIR tool, part of the digital P&R tool suite, can also be used in similar fashion, through dynamic scripting, to achieve "voltage-closure" or "current closure". This is particular useful in driving certain bias nodes in the analog circuits to target values.

In general, the output of the place and route tool is a GDS file that can then be verified from a physical standpoint with LVS (layout-vs.-schematic) and DRC (design rule check). Functionally, parasitics can be extracted from the GDS file, and the parasitic-extracted netlist should then be tested against the original circuit test benches to verify that performance degradation from layout parasitics is acceptable. If the performance is not acceptable, the parasitic-extracted netlist and the simulation results need to be examined closer to determine what exactly is causing the unacceptable behavior.

If poor behavior is observed, it must be due to some unexpected layout parasitic effect. The first thing to check is the circuit biases, and how they may have been affected by parasitic resistances. Examining the bias voltages in the circuit can point to the circuit nodes that have excessive voltage drops, or voltage mismatches with respect to the original schematic simulations. This can then be followed up with an examination of the resistance-only parasitic-extracted netlist, which should point to the layout segment that is creating the problem. The problem can then be fixed in the place and route tool through edits to the placement or routing constraints.

If the resistance examination does not reveal any issue, checking the capacitances would be next step. This time, a capacitance-only parasitic-extracted netlist can be examined to see if any non-bias nodes have unexpectedly large layout parasitic capacitance, and if these excess capacitances can explain the observed behavior. Once the problem is identified, the solution is the same as in the excess resistance case—addition of more placement and/or routing constraints for the place and route tool.

Another avenue by which parasitics can be controlled is through evaluation of many different layouts. This is only possible due to the speed at which layouts can be generated with the present invention's flow. Finally, once these parasitic effects are sufficiently controlled in one way or another so that the circuit performance is acceptable, and the layout passes DRC & LVS, then the design is complete.

Additional Stem Cell Methodology

In one embodiment, the following additional methodology for mixed-signal layout implementation using Stem Cells may be used to improve efficiency:

1. The Stem Cell Library Generator can minimize parasitic by fitting devices in the proper Nwell or Pwell stripes and using the power or ground net of the well. Parasitic to power or ground is generally minimized since the power or ground net will be used by a terminal of the cell. If a terminal of the stem cell should be routed to a power or ground, it would be better for the stem cell generator to create the terminal to power or ground connection internally in the cell rather than using external routing by digital P&R tool.
2. Users can add constraints to P&R tools or construct macros and array cell from base Stem Cells to increase matching and to reduce routing parasitics.
3. Electrical constraints can be provided or converted to physical constraints so Stem Cells and P&R tools will meet all EM-IR requirements. The stem cell generator and Array Cell generator can size internal pins and routing wires of the stem cell or array cell to meet the EM-IR of the pin.
4. An Array Cell generator is an intelligent macro compiler that can build multilevel recursive array such as composing a 768-finger mosfet into a two level (2×8)×(12×4) structure with the first level being a 2×8 array of unit finger and the second level being a 12×4 array containing first-level units which are 2×8 array of unit finger. The first-level 2×8 array can use small routing wire to connect to the small pins of the unit finger. The second-level 12×4 array can use larger routing wire to connect to the larger pin created by the first-level routing. If the 768-finger mosfet had been decomposed into a single level of 32×24 array using single-level routing, then only small and long routing wire can be used to connect to the small finger pin. The small routing wire may not meet the EM-IR requirement of the total array current.
5. The stem cell generator does not need to handle the additional complexity of creating arbitrarily large parallel devices. Instead, the macro and array cell generator can place and route array of unit Stem Cells efficiently to create large devices. The separation of features and division of labor in creating separate small stem cell generators and reusable large array cell generator decouple the DRC dependency greatly. A recursive multi-level array cell generator can be reused to construct array of any unit stem cell, so the stem cell generator does not need to create arbitrary large parallel devices.
6. The stem cell generator should not need to support odd-valued database-unit widths such as in channel lengths or in routing wire widths. Digital routers can only use even-valued database unit widths since there is no centerline for odd-database width. It is not necessary to support the odd width channel lengths such as 15 nm, 17 nm, and 19 nm. Foundries should reduce the database resolution instead of supporting odd-dbu widths. Supporting odd-dbu width will double the coding development cost without additional practical benefits for circuit design.
7. During the schematic design circuit exploration phase, the user should take advantage of layout knowledge provided by Stem Cells to make optimal layout choices rather than making suboptimal layout choices that waste area. Circuit exploration should choose device dimensions that are fast and area efficient. For example, mosfet layout should have the number of fins that provide the fastest transistor. Resistor and MosCap should have unit widths and unit lengths that maximize area usage. For example, due to power-supply gridding and routing wires, a MosCap can be between 10-fin to 16-fin, if a 16-fin MosCap gives better area utilization than a 10-fin MosCap, then circuit design should use the 16-fin MosCap rather than the 10-fin MosCap.
8. Similar to standard cell libraries, the Stem Cell Generator does not need to support all cell sizes or device sizes, or device sizes for which the Stem Cell Generator already has significantly better performing devices. For example, a MosCap with less than 4-fins will not be supported as these waste area, and a MosCap with over 16-fins will not be supported as these have comparable or faster performing devices that the Stem Cell Generator already supports.

As discussed above, one motivation behind the stem-cells innovation is to leverage the productivity of digital tools. Using this as the springboard, automatic optimization becomes the next front to be explored for another order of magnitude or more in productivity improvement. Just like in software, there is a need to move to a higher and higher level of abstraction once the lower levels have been taken care of, in this case via the stem-cells based methodology. Multi-objective optimization is the umbrella methodology to arrive at the target metrics or simply objectives against which the final layout will be will be measured. General objectives are performance, power, and area (PPA). In terms of performance, specific objectives could be speed/bandwidth, gain, and noise, etc. In order to meet these objectives, the multi-objective optimization flow provides rapid stepwise-refinement performance—cost tradeoff; in addition, each iterative solution must be virtually error-free. The discussion below will address aspects of the high-level multi-objective optimization flow.

A complete specification-to-layout repository framework that takes spec information, for instance circuit netlist, test benches, and allocated resources, from schematic designer, and automatically generate many optimized mixed-signal layouts with various performance profiles (due to layout-dependent effects). This enables schematic designer to perform system-level layout trade-off on mixed-signal circuit. The framework consists of multiple feedback loops, each has a different performance estimate accuracy. Accuracy is traded in for faster response time for the inner-most loop.

Inner-most loop—An automatic layout engine that combines analog constraints, Stem Cells and digital layout tools to automatically optimize for multiple performance objectives with a fast feedback loop. The objectives can be user-defined, or generated from input schematic and test bench. Using objectives as the criteria for layout quality avoids the pitfalls of pre-constraining the layout with heuristics traditionally, which is much more likely to lead to sub-optimal layout. Furthermore, using non-weighted objectives allows for layouts of different performance profiles to be put into the repository because weights are either subjective or require a great deal of manual interventions that may or may not pan out.

The objective function could easily define independent of circuit architecture, and the automatic layout engine will maintain an ever-improving set of layouts in terms of the multiple objectives defined.

Outer loop has higher accuracy and is used to adjust the objective function discussed above.

Users can define allocated resources for performing automatic layout and optimization, with which this methodology can automatically adjust the internal layout generation parameters.

Figure 14:
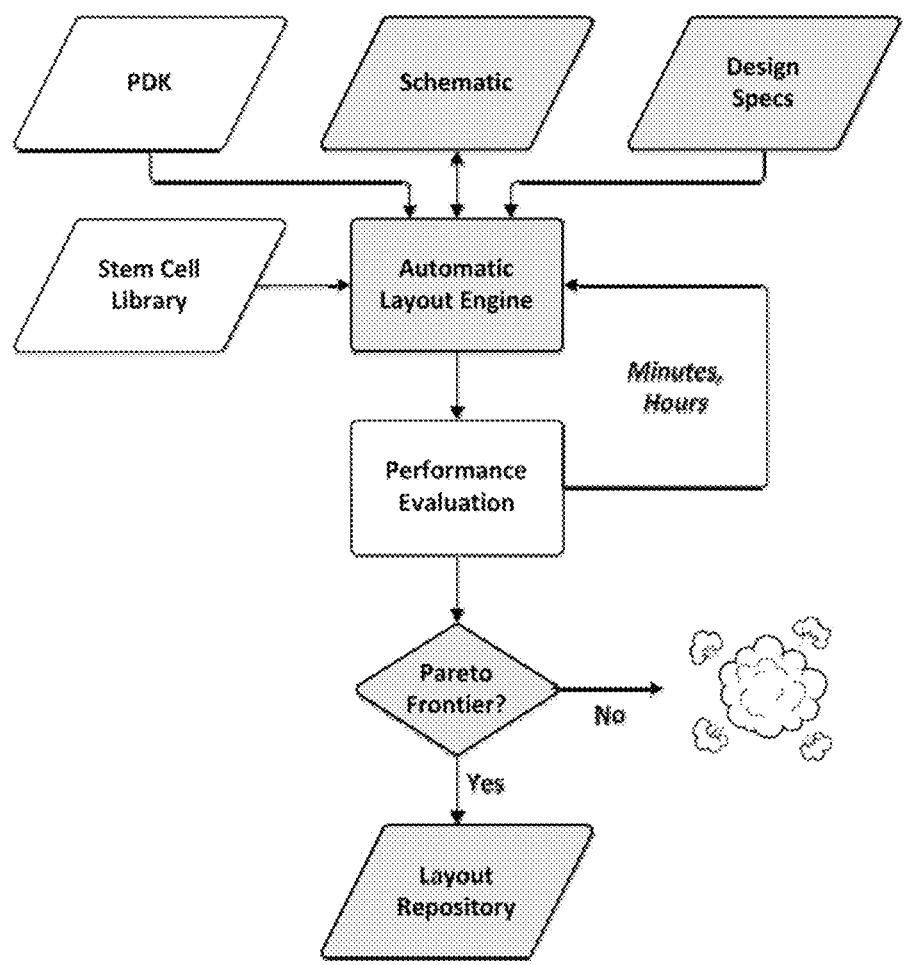
FIG. 14 shows an exemplary Block-Level Layout Optimization Flow according to one embodiment.
Figure 15:
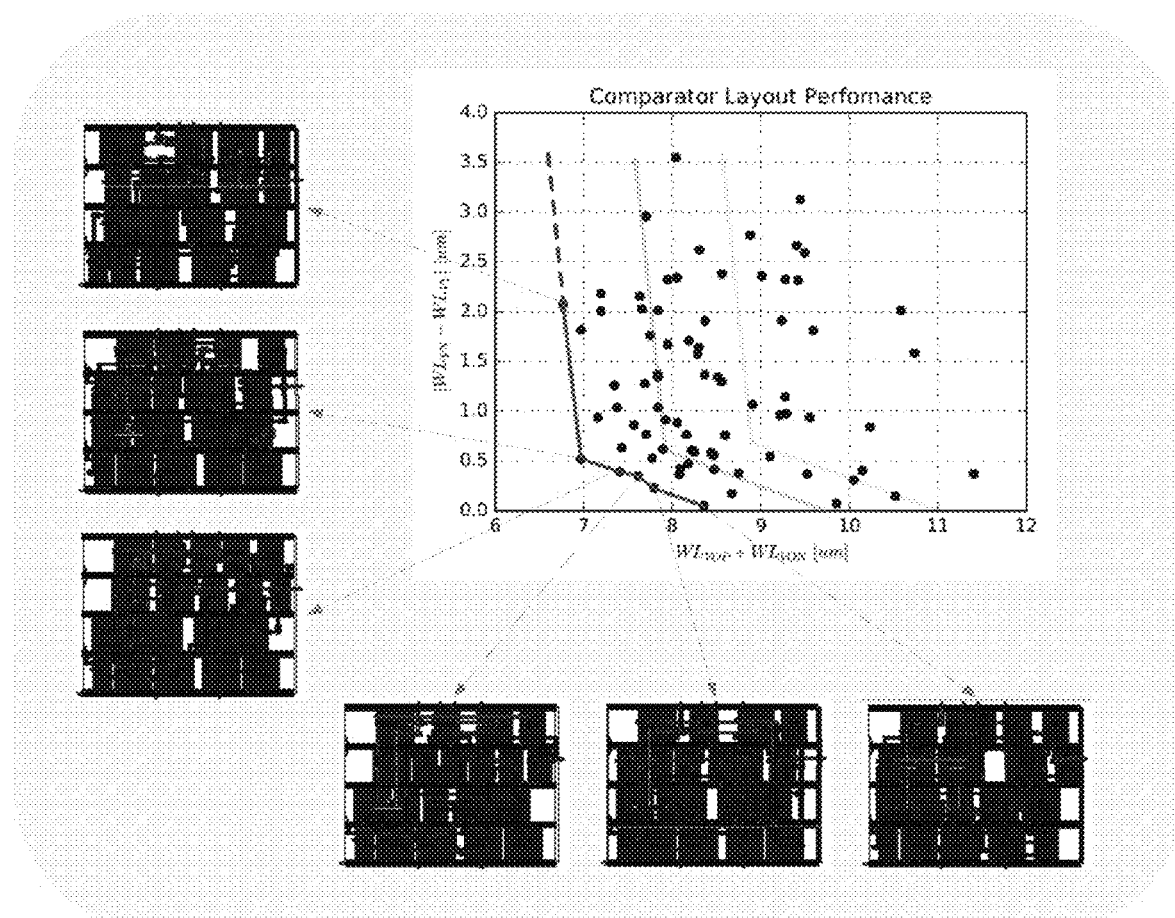
FIG. 15 shows an exemplary Pareto plot according to one embodiment.
Figure 16:
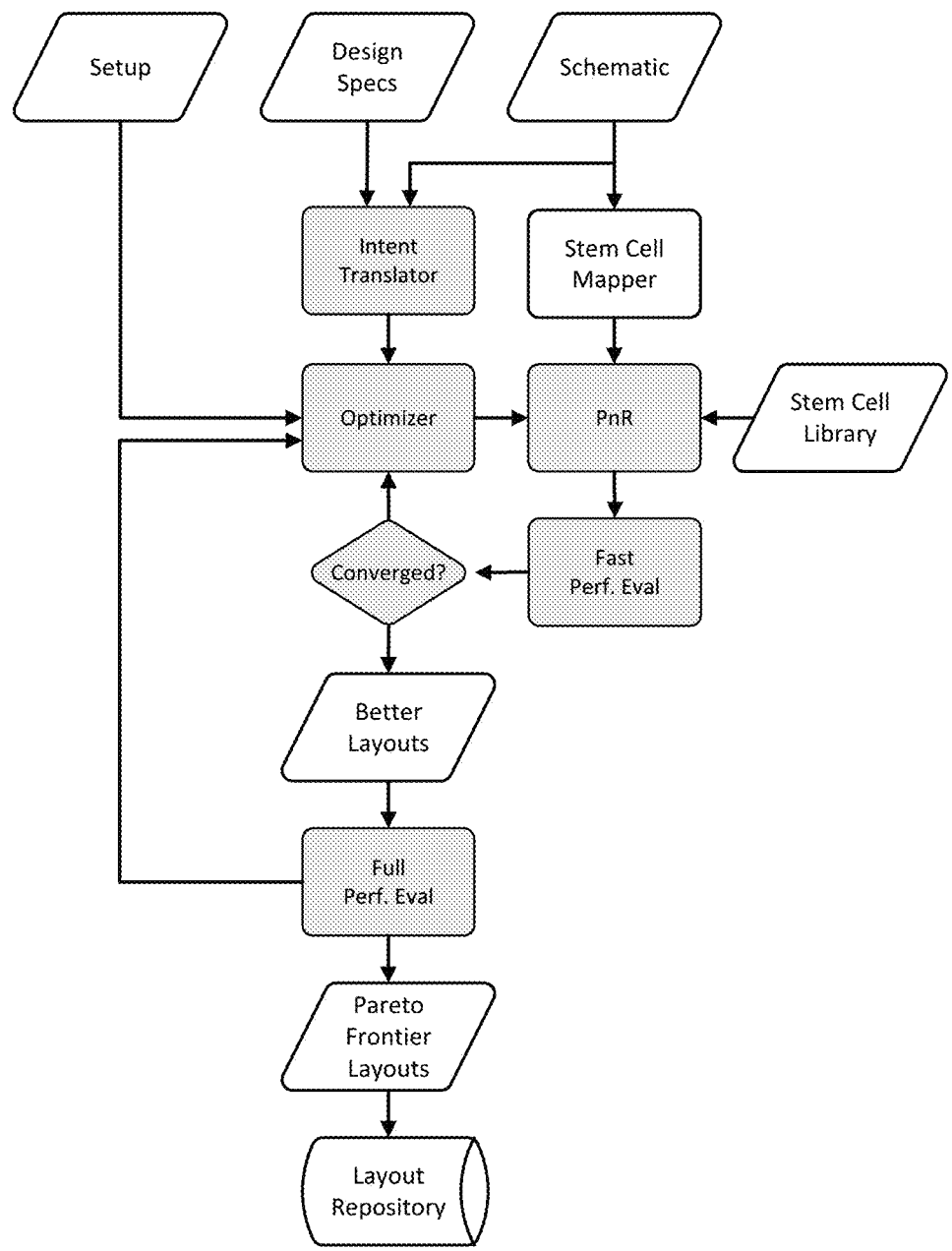
FIG. 16 shows an exemplary Detailed Layout Optimization Flow according to one embodiment.

FIG. 14 illustrates an exemplary Block-Level Layout Optimization Flow according to one embodiment. FIG. 16 shows an exemplary Detailed Layout Optimization Flow according to one embodiment. In general, there are many optimization choices, e.g. genetic algorithm, steepest-descent, neural network, fuzzy logic, etc. No matter what the choice is, a typical optimization result is illustrated by a Pareto plot shown in FIG. 15. The bottom left asymptote curve is generally referred to as the Pareto frontier and it is the where the metrics are closest to being met.

Using genetic algorithm as an example, from each iteration, many different layouts will be generated, PPA metrics are used to assess layout quality with control knobs or handles into the P&R tool flow (e.g. DEF):
Design dimensions
Pin attributes
Net attributes, e.g. net length
Component grouping, e block A is left of block B Only the layouts that are closest to the Pareto frontier will be as seeds to create the next generation of candidates and so forth. This and/or the aforementioned timing-driven flow are the means to optimize a layout to meet PPA metrics and other targets.

Static Vs Dynamic Stem Cell Library with Caching Solution

For digital P&R, a fixed standard-cell library is not only sufficient but also mandatory. Although a fixed standard-cell library is not comprehensive in terms of parametric coverage, e.g. providing a wide range of drive strength etc., its simplicity and ease-of-use is what lends to a rapid good-enough solution for most cases followed by subsequent refinements to improve PPA metrics.

As far as P&R tools are concerned, a stem sell is an analog standard cell indistinguishable from typical digital logic standard cells. Not surprisingly, a fixed stem-cell library must also be provided. Providing an enormous fixed size stem-cell library to comprehensively cover the analog design space is not only impractical because of what is known as the curse of the combinations. It would necessitate millions of cells, a consequence of explosive combination of different numbers of rows, fins, fingers, and variants such as p- or n-type and implants, just for one tech node, and compliant with only one standard cell library, e.g. 9-track PODE. It is both cost- and time-prohibitive.

Figure 17:
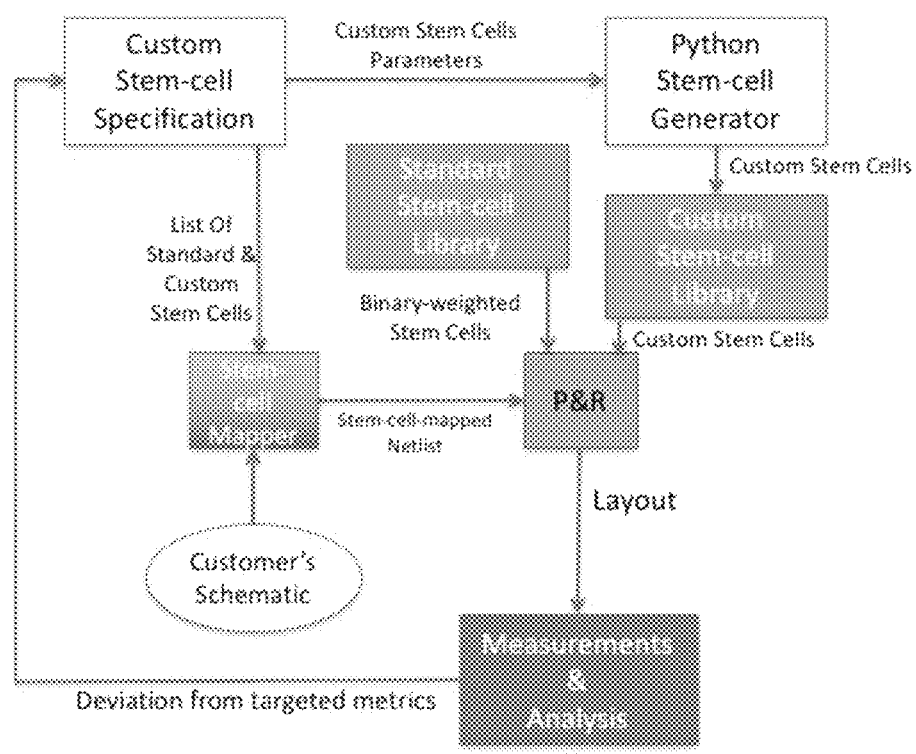
FIG. 17 shows an exemplary Just-in-Time Stem-Cell Library according to one embodiment.

Furthermore, the P&R operation will be slowed down because of the large library size. From an ROI standpoint, most of the library Stem Cells will never be used at all, making the generation cost unjustifiable. The way around this is to supplement the fixed stem-cell library with a dynamic, just-in-time, on-the-fly stem-cell library (as shown in FIG. 17). For example, at the end of each iteration of P&R, an extra stem-cell library, in additional to the fixed library, could be generated with all the new Stem Cells that will be required in the next iteration. This new library will appear as a fixed library to P&R because its creation or updates are done in between iterations.

In operation, the very first P&R iteration uses the fixed stem-cell library with binary-weighted finger numbers along with most-used channel lengths and fin numbers which guarantee:
DRC-clean abutment with any other Stem Cells or standard cells.
Superior gap-filling and dense clustering compared to the large macro's
Alignment to standard cell grid.

Note that this is achieved by surrounding each stem cell device core with dummy abutment structures in layout which unfortunately incur an area penalty. This will be mitigated in the next iteration when neighboring Stem Cells of the same kind could be merged, or clustered into a rectangular array, to improve the area efficiency, e.g. nf2+nf8+nf16 becomes a single-row stem cell nf26 or a double-row 2×nf13. This begs a question—why not use the merged or array-clustered Stem Cells at the very beginning. The reason is that the aspect ratio of the merged or clustered array is not known at the first iteration; it is only after the $1^{st}$ P&R that we can infer an approximate outline and merge the loose cluster into a tight rectangular array. This type of merging is simply replacing a cluster of initial-placed binary-weighted Stem Cells with a dynamically-generated stem cell followed by inserting it into the supplemental library, akin to the memory caching model of CPU, a merged stem cell (a piece of cached-missed data) will automatically be provided by the dynamic library generator (caching memory manager).

Even more important, the schematic of a design is usually the golden reference. Approximate stem-cell mapping is not likely an option—all the L's and W's have to match exactly before and after layout with schematic. In other words, the stem-cell-mapped netlist and subsequently the stem-cell-based layout must pass SVS/LVS with the original schematic. This is another compelling reason of why there should be a virtually limitless library to fulfill this need, and hence the supplementary dynamic library.

Figure 12:
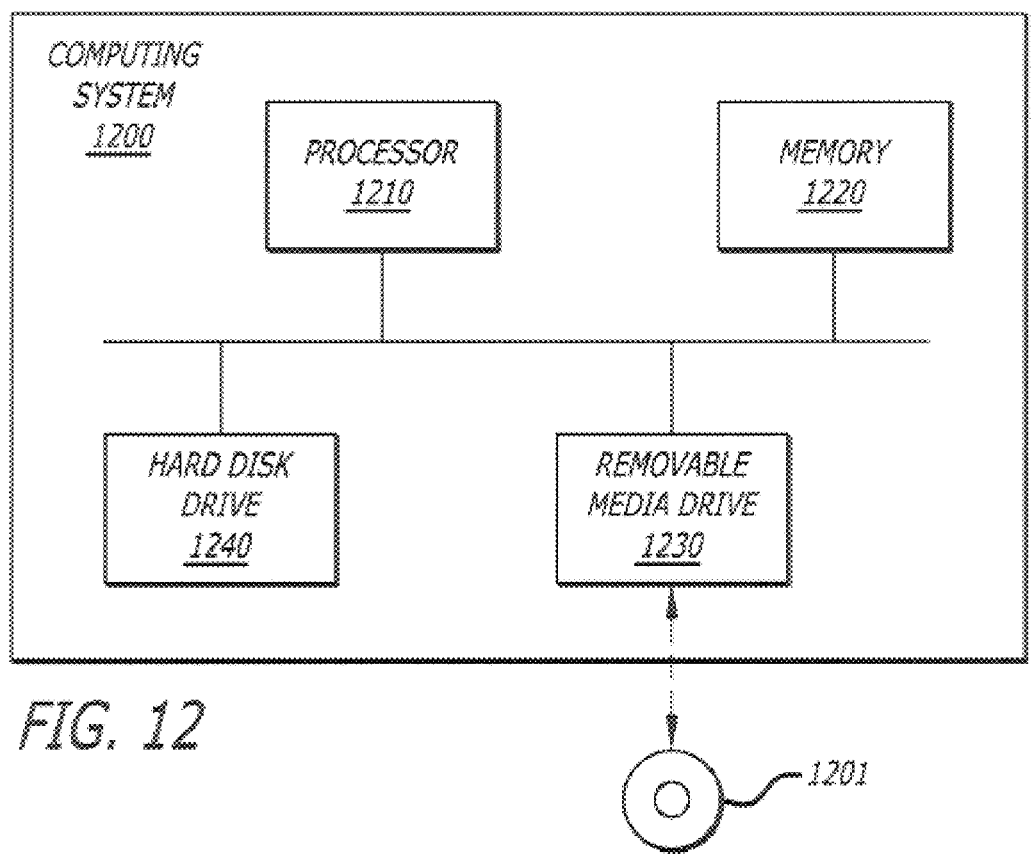
FIG. 12 illustrates a computing system that may be used to perform some or all of the processes in accordance with a number of embodiments of the invention.

Referring now to FIG. 12, a computing system 1200 is illustrated that may be used to perform some or all of the processes in accordance with a number of embodiments of the invention. In one embodiment of the invention, the computing system 1200 includes a processor 1210, a memory 1220, a removable media drive 1230, and a hard disk drive 1240. In one embodiment, the processor 1210 executes instructions residing on a machine-readable medium, such as the hard disk drive 1240, a removable medium (e.g., an optical medium (compact disk (CD), digital video disk (DVD), etc.), a magnetic medium (magnetic disk, a magnetic tape, etc.), or a combination of both. The instructions may be loaded from the machine-readable medium into the memory 1220, which may include Random Access Memory (RAM), dynamic RAM (DRAM), etc. The processor 1210 may retrieve the instructions from the memory 1220 and execute the instructions to perform the operations described above.

Note that any or all of the components and the associated hardware illustrated in FIG. 12 may be used in various embodiments of the system 1200. However, it should be appreciated that other configurations of the system 1200 may include more or less devices than those shown in FIG. 12.

Some portions of the preceding detailed description have been presented in terms of algorithms and symbolic representations of operations on data bits within a computer memory. These algorithmic descriptions and representations are the tools used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be kept in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The embodiments of the invention also relates to an apparatus for performing the operations described herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The processes and displays presented herein are not inherently related to any particular computer or other apparatus. Various general-purpose systems may be used with programs in accordance with the teachings herein, or it may prove convenient to construct a more specialized apparatus to perform the operations described. The required structure for a variety of these systems will appear from the description below. In addition, the embodiments of the invention are not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.).

In addition, while the system and method to optimize a layout based on the yield analysis is disclosed by reference to the various embodiments and examples detailed above, it should be understood that these examples are intended in an illustrative rather than limiting sense, as it is contemplated that modifications will readily occur to those skilled in the art which are intended to fall within the scope of the present invention.

While the invention has been described in connection with various aspects, it will be understood that the invention is capable of further modifications. This application is intended to cover any variations, uses or adaptation of the invention following, in general, the principles of the invention, and including such departures from the present disclosure as come within the known and customary practice within the art to which the invention pertains.

The invention claimed is:

1. A method for designing an analog and mixed-signal integrated circuit layout, the method comprising:
   generating a stem cell library with stem cell layouts used to design the analog and mixed-signal integrated circuit layout, wherein each stem cell layout includes an analog core area where an analog device element resides, a framing area having a ring of alternating minimum sized gate-type material and diffusion-type material, and abutment boundaries on left, right, top, and bottom sides of the analog core area;
   mapping device elements in a schematic netlist to the stem cell layouts in the stem cell library; and
   placing and routing the mapped device elements to optimize a layout for the schematic netlist.

2. The method of claim 1, wherein the analog device element residing in the analog core area of the stem cell layout is a transistor, a resistor, a capacitor, a MOSFET, or any other analog devices.

3. The method of claim 1, wherein each abutment boundary is an empty space or a fill pattern that allows cells within a same voltage domain to abut without violating any Design Rule Checks (DRC).

4. The method of claim 1, wherein the stem cell library includes static stem cells with frequently used lengths and widths for use by many designs without knowing each design ahead of time.

5. The method of claim 1, where in the stem cell library includes dynamic stem cells that are design-specific cells and that are generated dynamically.

6. The method of claim 1, further comprising:
mapping the device elements in the schematic netlist to the stem cell layouts by selecting static stem cell layouts with closest sizes of the device elements.

7. The method of claim 1, further comprising:
mapping the device elements in the schematic netlist to the stem cell layouts by generating dynamic stem cell layouts that match the device elements.

8. The method of claim 1, further comprising:
pre-processing the device elements in the schematic netlist to merge some device elements into a bigger device to reduce number of device elements and layout size.

9. The method of claim 1, further comprising:
placing and routing the mapped device elements using pin placement information to optimize a layout for the schematic netlist.

10. The method of claim 3, further comprising:
optimizing the layout for the schematic netlist using a Pareto plot.

11. A system for designing an analog and mixed-signal integrated circuit layout, the system comprising:
a stem cell library generator that generates a stem cell library with stem cell layouts used to design the analog and mixed-signal integrated circuit layout, wherein each stem cell layout includes an analog core area where an analog device element resides, a framing area having a ring of alternating minimum sized gate-type material and diffusion-type material, and abutment boundaries on left, right, top, and bottom sides of the analog core area;
a netlist mapper that maps device elements in a schematic netlist to the stem cell layouts in the stem cell library; and
a place-and-route tool suite that places and routes the mapped device elements to optimize a layout for the schematic netlist.

12. The system of claim 11, wherein the analog device element residing in the analog core area of the stem cell layout is a transistor, a resistor, a capacitor, a MOSFET, or any other analog devices.

13. The system of claim 11, wherein each abutment boundary is an empty space or a fill pattern that allows cells within a same voltage domain to abut without violating any Design Rule Checks (DRC).

14. The system of claim 11, wherein the stem cell library includes static stem cells with frequently used lengths and widths for use by many designs without knowing each design ahead of time.

15. The system of claim 11, where in the stem cell library includes dynamic stem cells that are design-specific cells and that are generated dynamically.

16. The system of claim 11, wherein the netlist mapper maps the device elements in the schematic netlist to the stem cell layouts by selecting static stem cell layouts with closest sizes of the device elements.

17. The system of claim 11, wherein the netlist mapper maps the device elements in the schematic netlist to the stem cell layouts by generating dynamic stem cell layouts that match the device elements.

18. The system of claim 11, wherein the netlist mapper pre-processes the device elements in the schematic netlist to merge some device elements into a bigger device to reduce number of device elements and layout size.

19. The system of claim 11, wherein the place-and-route module places and routes the mapped device elements using pin placement information to optimize the layout for the schematic netlist.

20. The system of claim 11, wherein the place-and-route module optimizes the layout for the schematic netlist using a Pareto plot.

* * * * *